US008663645B2

(12) United States Patent
Kosmatopoulos

(10) Patent No.: US 8,663,645 B2
(45) Date of Patent: Mar. 4, 2014

(54) USE OF NATIVE PEPTIDES AND THEIR OPTIMIZED DERIVATIVES FOR VACCINATION

(75) Inventor: Kostantinos (Kostas) Kosmatopoulos, Paris (FR)

(73) Assignee: Vaxon Biotech, Evry Cedex (FR)

( * ) Notice: Subject to any disclaimer, the term of this patent is extended or adjusted under 35 U.S.C. 154(b) by 776 days.

(21) Appl. No.: 11/913,138

(22) PCT Filed: May 9, 2006

(86) PCT No.: PCT/EP2006/005325

§ 371 (c)(1),
(2), (4) Date: Nov. 28, 2007

(87) PCT Pub. No.: WO2006/120038

PCT Pub. Date: Nov. 16, 2006

(65) Prior Publication Data

US 2008/0254051 A1 Oct. 16, 2008

(30) Foreign Application Priority Data

May 9, 2005 (EP) .................................... 05290984

(51) Int. Cl.
*A61K 39/00* (2006.01)
*A61K 39/12* (2006.01)
*A61K 38/00* (2006.01)
*A61K 38/08* (2006.01)

(52) U.S. Cl.
USPC .................. 424/185.1; 424/186.1; 424/277.1; 514/1.1

(58) Field of Classification Search
None
See application file for complete search history.

(56) References Cited

U.S. PATENT DOCUMENTS

| | | | | |
|---|---|---|---|---|
| 7,419,669 | B2 * | 9/2008 | Kosmatopoulos et al. | 424/184.1 |
| 7,425,606 | B2 * | 9/2008 | Kosmatopoulos et al. | 530/300 |
| 2003/0157135 | A1 * | 8/2003 | Tsuji et al. | 424/278.1 |
| 2004/0072240 | A1 * | 4/2004 | Kosmatopoulos et al. | 435/7.1 |

FOREIGN PATENT DOCUMENTS

| | | | |
|---|---|---|---|
| WO | WO 01/60391 | * | 8/2001 |
| WO | WO 02/08716 | | 1/2002 |
| WO | WO 03/091383 | | 11/2003 |

OTHER PUBLICATIONS

Woodberry et al., Journal of Virology, 1999, 73(7):5320-532.*

International Search Report and Written Opinion for PCT/EP2006/005325 filed May 9, 2006.

Tourdot S et al: "A general strategy to enhance immunogenicity of low-affinity HLA-A2. 1-associated peptides: implication of the identification of cryptic tumor epitopes."European Journal of Immunology Dec. 2000, vol. 30, No. 12, Dec. 2000, pp. 3422-3421, XP0024630145.

Hoffmann T K et al: "The ability of variant peptides to reverse the nonresponsiveness of T lymphocytes to the wild-type sequence p53264-272 epitope." Journal of Immunology Feb. 1, 2002 United States, vol. 168, No. 3, Feb. 1, 2002, pp. 1338-1347, XP002430146.

Scardino Antonio et al: "HER-2/neu and hTERT crysptic epitopes as novel targets for broad spectrum tumor immunotherapy." Journal of Immunology (Baltimore, MD.: 1950) Jun. 1, 2002, vol. 168, No. 11, Jun. 1, 2002, pp. 5900-5906, XP002430147.

Gross David-Alexandre et al: "High vaccination efficiency of low-affinity epitopes in antitumor immunotherapy." The Journal of Clinical Investigation Feb. 2004, vol. 113, No. 3, Feb. 2004, pp. 425-433, XP002430148.

Sette A et al: "Epitope-based vaccines: an update on epitope identification, vaccine design and delivery." Current Opinion in Immunology, Elsevier, Oxford, GB, vol. 15, No. 4, Jun. 2003, pp. 461-470, XP004444354.

Gross David-Alexandre et al: "High Vaccination Efficiency of Low-Affinity Epitopes in Antitumor Immunotherapy," The Journal of Clinical Investigation Feb. 2004, vol. 113, No. 3, Feb. 2004, pp. 425-433.

Bins Adriaan et al: "Phase I Clinical Study With Multiple Peptide Vaccines in Combination With Tetanus Toxoid and GM-CSF in Advanced-stage HLA-A*0201-positive Melanoma Patients,"Journal of Immunotherapy Feb./Mar. 2007, vol. 30, No. 2, Feb./Mar. 2007, pp. 234-239.

Rosenberg Steven A et al: "Different Adjuvanticity of Incomplete Freund's Adjuvant Derived From Beef or Vegetable Components in Melanoma Patients Immunized With a Peptide Vaccine," Journal of Immunotherapy Jul./Aug. 2010, vol. 33, No. 6, Jul./Aug. 2010, pp. 626-629.

Hodi F. Stephen MD et al: "Improved Survival with Ipilimumab in Patients with Metastatic Melanoma," The New England Journal of Medicine, Aug. 19, 2010, vol. 363, No. 8, Aug. 19, 2010, pp. 711-723.

* cited by examiner

*Primary Examiner* — Nicole Kinsey White
(74) *Attorney, Agent, or Firm* — Alston & Bird

(57) ABSTRACT

The present invention pertains to the field of vaccination, and more particularly to the fields of antitumor and antiviral vaccination. The invention relates to the use of a native peptide in a medicinal composition, for selecting and/or boosting part of a CTL immune response which has been initiated by an optimized immunogenic peptide derived from said native peptide. The invention also concerns vaccination kits which comprise several doses of optimized peptides and of their cognate native peptides.

9 Claims, 4 Drawing Sheets

SEQUENCE LISTING

```
<160> NUMBER OF SEQ ID NOS: 92

<210> SEQ ID NO 1
<211> LENGTH: 9
<212> TYPE: PRT
<213> ORGANISM: Artificial
<220> FEATURE:
<223> OTHER INFORMATION: TERT-572

<400> SEQUENCE: 1

Arg Leu Phe Phe Tyr Arg Lys Ser Val
1               5


<210> SEQ ID NO 2
<211> LENGTH: 9
<212> TYPE: PRT
<213> ORGANISM: Artificial
<220> FEATURE:
<223> OTHER INFORMATION: TERT-572Y1
```

<400> SEQUENCE: 2

Tyr Leu Phe Phe Tyr Arg Lys Ser Val
1 5

<210> SEQ ID NO 3
<211> LENGTH: 10
<212> TYPE: PRT
<213> ORGANISM: Artificial
<220> FEATURE:
<223> OTHER INFORMATION: TERT-988

<400> SEQUENCE: 3

Asp Leu Gln Val Asn Ser Leu Gln Thr Val
1 5 10

<210> SEQ ID NO 4
<211> LENGTH: 10
<212> TYPE: PRT
<213> ORGANISM: Artificial
<220> FEATURE:
<223> OTHER INFORMATION: TERT-988Y1

<400> SEQUENCE: 4

Tyr Leu Gln Val Asn Ser Leu Gln Thr Val
1 5 10

<210> SEQ ID NO 5
<211> LENGTH: 9
<212> TYPE: PRT
<213> ORGANISM: Artificial
<220> FEATURE:
<223> OTHER INFORMATION: MAGE-A-248D9

<400> SEQUENCE: 5

Tyr Leu Glu Tyr Arg Gln Val Pro Asp
1 5

<210> SEQ ID NO 6
<211> LENGTH: 9
<212> TYPE: PRT
<213> ORGANISM: Artificial
<220> FEATURE:
<223> OTHER INFORMATION: MAGE-A-248V9

<400> SEQUENCE: 6

Tyr Leu Glu Tyr Arg Gln Val Pro Val
1 5

<210> SEQ ID NO 7
<211> LENGTH: 9
<212> TYPE: PRT
<213> ORGANISM: Artificial
<220> FEATURE:
<223> OTHER INFORMATION: MAGE-A-248G9

<400> SEQUENCE: 7

Tyr Leu Glu Tyr Arg Gln Val Pro Gly
1 5

<210> SEQ ID NO 8
<211> LENGTH: 9
<212> TYPE: PRT
<213> ORGANISM: Artificial
<220> FEATURE:
<223> OTHER INFORMATION: Gp100-154

<400> SEQUENCE: 8

Lys Thr Trp Gly Gln Tyr Trp Gln Val
1               5

<210> SEQ ID NO 9
<211> LENGTH: 9
<212> TYPE: PRT
<213> ORGANISM: Artificial
<220> FEATURE:
<223> OTHER INFORMATION: Gp100-154Y1

<400> SEQUENCE: 9

Tyr Thr Trp Gly Gln Tyr Trp Gln Val
1               5

<210> SEQ ID NO 10
<211> LENGTH: 9
<212> TYPE: PRT
<213> ORGANISM: Artificial
<220> FEATURE:
<223> OTHER INFORMATION: Gp100-154M155

<400> SEQUENCE: 10

Lys Met Trp Gly Gln Tyr Trp Gln Val
1               5

<210> SEQ ID NO 11
<211> LENGTH: 9
<212> TYPE: PRT
<213> ORGANISM: Artificial
<220> FEATURE:
<223> OTHER INFORMATION: FluM-58

<400> SEQUENCE: 11

Gly Ile Gly Leu Phe Val Phe Thr Leu
1               5

<210> SEQ ID NO 12
<211> LENGTH: 9
<212> TYPE: PRT
<213> ORGANISM: Artificial
<220> FEATURE:
<223> OTHER INFORMATION: FluM-58Y1

<400> SEQUENCE: 12

Tyr Ile Gly Leu Phe Val Phe Thr Leu
1               5

<210> SEQ ID NO 13
<211> LENGTH: 9
<212> TYPE: PRT
<213> ORGANISM: Artificial
<220> FEATURE:
<223> OTHER INFORMATION: HIVgag-76

<400> SEQUENCE: 13

Ser Leu Tyr Asn Thr Val Ala Thr Leu
1               5

<210> SEQ ID NO 14
<211> LENGTH: 9
<212> TYPE: PRT
<213> ORGANISM: Artificial
<220> FEATURE:
<223> OTHER INFORMATION: HIVgag-76Y1

<400> SEQUENCE: 14

Tyr Leu Tyr Asn Thr Val Ala Thr Leu
1 5

<210> SEQ ID NO 15
<211> LENGTH: 9
<212> TYPE: PRT
<213> ORGANISM: Artificial
<220> FEATURE:
<223> OTHER INFORMATION: HBVpol-575

<400> SEQUENCE: 15

Phe Leu Leu Ser Leu Gly Ile His Leu
1 5

<210> SEQ ID NO 16
<211> LENGTH: 9
<212> TYPE: PRT
<213> ORGANISM: Artificial
<220> FEATURE:
<223> OTHER INFORMATION: HBVpol-575Y1

<400> SEQUENCE: 16

Tyr Leu Leu Ser Leu Gly Ile His Leu
1 5

<210> SEQ ID NO 17
<211> LENGTH: 10
<212> TYPE: PRT
<213> ORGANISM: Artificial
<220> FEATURE:
<223> OTHER INFORMATION: HBVpol-765

<400> SEQUENCE: 17

Leu Leu Gly Cys Ala Ala Asn Trp Ile Leu
1 5 10

<210> SEQ ID NO 18
<211> LENGTH: 10
<212> TYPE: PRT
<213> ORGANISM: Artificial
<220> FEATURE:
<223> OTHER INFORMATION: HBVpol-765Y1

<400> SEQUENCE: 18

Tyr Leu Gly Cys Ala Ala Asn Trp Ile Leu
1 5 10

<210> SEQ ID NO 19
<211> LENGTH: 9
<212> TYPE: PRT
<213> ORGANISM: Artificial
<220> FEATURE:
<223> OTHER INFORMATION: Mart-1-27

<400> SEQUENCE: 19

Ala Ala Gly Ile Gly Ile Leu Thr Val
1 5

<210> SEQ ID NO 20
<211> LENGTH: 9
<212> TYPE: PRT
<213> ORGANISM: Artificial
<220> FEATURE:
<223> OTHER INFORMATION: Mart-1-27Y1

<400> SEQUENCE: 20

Tyr Ala Gly Ile Gly Ile Leu Thr Val
1               5

<210> SEQ ID NO 21
<211> LENGTH: 10
<212> TYPE: PRT
<213> ORGANISM: Artificial
<220> FEATURE:
<223> OTHER INFORMATION: Mart-1-26

<400> SEQUENCE: 21

Glu Ala Ala Gly Ile Gly Ile Leu Thr Val
1               5                   10

<210> SEQ ID NO 22
<211> LENGTH: 10
<212> TYPE: PRT
<213> ORGANISM: Artificial
<220> FEATURE:
<223> OTHER INFORMATION: Mart-1-26L27

<400> SEQUENCE: 22

Glu Leu Ala Gly Ile Gly Ile Leu Thr Val
1               5                   10

<210> SEQ ID NO 23
<211> LENGTH: 10
<212> TYPE: PRT
<213> ORGANISM: Artificial
<220> FEATURE:
<223> OTHER INFORMATION: Gp100-177

<400> SEQUENCE: 23

Ala Met Leu Gly Thr His Thr Met Glu Val
1               5                   10

<210> SEQ ID NO 24
<211> LENGTH: 10
<212> TYPE: PRT
<213> ORGANISM: Artificial
<220> FEATURE:
<223> OTHER INFORMATION: Gp100-177Y1

<400> SEQUENCE: 24

Tyr Met Leu Gly Thr His Thr Met Glu Val
1               5                   10

<210> SEQ ID NO 25
<211> LENGTH: 9
<212> TYPE: PRT
<213> ORGANISM: Artificial
<220> FEATURE:
<223> OTHER INFORMATION: Gp100-178

<400> SEQUENCE: 25

Met Leu Gly Thr His Thr Met Glu Val
1               5

<210> SEQ ID NO 26
<211> LENGTH: 9
<212> TYPE: PRT
<213> ORGANISM: Artificial
<220> FEATURE:
<223> OTHER INFORMATION: Gp100-178Y1

<400> SEQUENCE: 26

Tyr Leu Gly Thr His Thr Met Glu Val
1 5

<210> SEQ ID NO 27
<211> LENGTH: 10
<212> TYPE: PRT
<213> ORGANISM: Artificial
<220> FEATURE:
<223> OTHER INFORMATION: Gp100-570

<400> SEQUENCE: 27

Ser Leu Ala Asp Thr Asn Ser Leu Ala Val
1 5 10

<210> SEQ ID NO 28
<211> LENGTH: 10
<212> TYPE: PRT
<213> ORGANISM: Artificial
<220> FEATURE:
<223> OTHER INFORMATION: Gp100-570Y1

<400> SEQUENCE: 28

Tyr Leu Ala Asp Thr Asn Ser Leu Ala Val
1 5 10

<210> SEQ ID NO 29
<211> LENGTH: 8
<212> TYPE: PRT
<213> ORGANISM: Artificial
<220> FEATURE:
<223> OTHER INFORMATION: Gp100-209

<400> SEQUENCE: 29

Thr Asp Gln Val Pro Phe Ser Val
1 5

<210> SEQ ID NO 30
<211> LENGTH: 8
<212> TYPE: PRT
<213> ORGANISM: Artificial
<220> FEATURE:
<223> OTHER INFORMATION: Gp100-209Y1

<400> SEQUENCE: 30

Tyr Asp Gln Val Pro Phe Ser Val
1 5

<210> SEQ ID NO 31
<211> LENGTH: 8
<212> TYPE: PRT
<213> ORGANISM: Artificial
<220> FEATURE:
<223> OTHER INFORMATION: Gp100-209M210

<400> SEQUENCE: 31

Tyr Met Gln Val Pro Phe Ser Val
1 5

<210> SEQ ID NO 32
<211> LENGTH: 10
<212> TYPE: PRT
<213> ORGANISM: Artificial
<220> FEATURE:
<223> OTHER INFORMATION: Gp100-476

<400> SEQUENCE: 32

Val Leu Tyr Arg Tyr Gly Ser Phe Ser Val
1 5 10

<210> SEQ ID NO 33
<211> LENGTH: 10
<212> TYPE: PRT
<213> ORGANISM: Artificial
<220> FEATURE:
<223> OTHER INFORMATION: Gp100-476Y1

<400> SEQUENCE: 33

Tyr Leu Tyr Arg Tyr Gly Ser Phe Ser Val
1 5 10

<210> SEQ ID NO 34
<211> LENGTH: 10
<212> TYPE: PRT
<213> ORGANISM: Artificial
<220> FEATURE:
<223> OTHER INFORMATION: Gp100-457

<400> SEQUENCE: 34

Leu Leu Asp Gly Thr Ala Thr Leu Arg Leu
1 5 10

<210> SEQ ID NO 35
<211> LENGTH: 10
<212> TYPE: PRT
<213> ORGANISM: Artificial
<220> FEATURE:
<223> OTHER INFORMATION: Gp100-457Y1

<400> SEQUENCE: 35

Tyr Leu Asp Gly Thr Ala Thr Leu Arg Leu
1 5 10

<210> SEQ ID NO 36
<211> LENGTH: 9
<212> TYPE: PRT
<213> ORGANISM: Artificial
<220> FEATURE:
<223> OTHER INFORMATION: HER-2/neu-799

<400> SEQUENCE: 36

Gln Leu Met Pro Tyr Gly Cys Leu Leu
1 5

<210> SEQ ID NO 37
<211> LENGTH: 9
<212> TYPE: PRT
<213> ORGANISM: Artificial
<220> FEATURE:
<223> OTHER INFORMATION: HER-2/neu-799Y1

<400> SEQUENCE: 37

Tyr Leu Met Pro Tyr Gly Cys Leu Leu
1 5

<210> SEQ ID NO 38
<211> LENGTH: 9
<212> TYPE: PRT
<213> ORGANISM: Artificial
<220> FEATURE:
<223> OTHER INFORMATION: HER-2/neu-369

<400> SEQUENCE: 38

Lys Ile Phe Gly Ser Leu Ala Phe Leu
1               5

<210> SEQ ID NO 39
<211> LENGTH: 9
<212> TYPE: PRT
<213> ORGANISM: Artificial
<220> FEATURE:
<223> OTHER INFORMATION: HER-2/neu-369Y1

<400> SEQUENCE: 39

Tyr Ile Phe Gly Ser Leu Ala Phe Leu
1               5

<210> SEQ ID NO 40
<211> LENGTH: 9
<212> TYPE: PRT
<213> ORGANISM: Artificial
<220> FEATURE:
<223> OTHER INFORMATION: HER-2/neu-789

<400> SEQUENCE: 40

Cys Leu Thr Ser Thr Val Gln Leu Val
1               5

<210> SEQ ID NO 41
<211> LENGTH: 9
<212> TYPE: PRT
<213> ORGANISM: Artificial
<220> FEATURE:
<223> OTHER INFORMATION: HER-2/neu-789Y1

<400> SEQUENCE: 41

Tyr Leu Thr Ser Thr Val Gln Leu Val
1               5

<210> SEQ ID NO 42
<211> LENGTH: 8
<212> TYPE: PRT
<213> ORGANISM: Artificial
<220> FEATURE:
<223> OTHER INFORMATION: HER-2/neu-48

<400> SEQUENCE: 42

His Leu Tyr Gln Gly Cys Gln Trp
1               5

<210> SEQ ID NO 43
<211> LENGTH: 8
<212> TYPE: PRT
<213> ORGANISM: Artificial
<220> FEATURE:
<223> OTHER INFORMATION: HER-2/neu-48Y1

<400> SEQUENCE: 43

Tyr Leu Tyr Gln Gly Cys Gln Trp
1               5

<210> SEQ ID NO 44
<211> LENGTH: 10
<212> TYPE: PRT
<213> ORGANISM: Artificial
<220> FEATURE:
<223> OTHER INFORMATION: HER-2/neu-773

<400> SEQUENCE: 44

Val Met Ala Gly Val Gly Ser Pro Tyr Val
1 5 10

<210> SEQ ID NO 45
<211> LENGTH: 10
<212> TYPE: PRT
<213> ORGANISM: Artificial
<220> FEATURE:
<223> OTHER INFORMATION: HER-2/neu-773Y1

<400> SEQUENCE: 45

Tyr Met Ala Gly Val Gly Ser Pro Tyr Val
1 5 10

<210> SEQ ID NO 46
<211> LENGTH: 8
<212> TYPE: PRT
<213> ORGANISM: Artificial
<220> FEATURE:
<223> OTHER INFORMATION: HER-2/neu-5

<400> SEQUENCE: 46

Ala Leu Cys Arg Trp Gly Leu Leu
1 5

<210> SEQ ID NO 47
<211> LENGTH: 8
<212> TYPE: PRT
<213> ORGANISM: Artificial
<220> FEATURE:
<223> OTHER INFORMATION: HER-2/neu-5Y1

<400> SEQUENCE: 47

Tyr Leu Cys Arg Trp Gly Leu Leu
1 5

<210> SEQ ID NO 48
<211> LENGTH: 9
<212> TYPE: PRT
<213> ORGANISM: Artificial
<220> FEATURE:
<223> OTHER INFORMATION: HER-2/neu-851

<400> SEQUENCE: 48

Val Leu Val Lys Ser Pro Asn His Val
1 5

<210> SEQ ID NO 49
<211> LENGTH: 9
<212> TYPE: PRT
<213> ORGANISM: Artificial
<220> FEATURE:
<223> OTHER INFORMATION: HER-2/neu-851Y1

<400> SEQUENCE: 49

Tyr Leu Val Lys Ser Pro Asn His Val
1 5

<210> SEQ ID NO 50
<211> LENGTH: 9
<212> TYPE: PRT
<213> ORGANISM: Artificial
<220> FEATURE:
<223> OTHER INFORMATION: HER-2/neu-661

<400> SEQUENCE: 50

Ile Leu Leu Val Val Val Leu Gly Val
1               5

<210> SEQ ID NO 51
<211> LENGTH: 9
<212> TYPE: PRT
<213> ORGANISM: Artificial
<220> FEATURE:
<223> OTHER INFORMATION: HER-2/neu-661Y1

<400> SEQUENCE: 51

Tyr Leu Leu Val Val Val Leu Gly Val
1               5

<210> SEQ ID NO 52
<211> LENGTH: 9
<212> TYPE: PRT
<213> ORGANISM: Artificial
<220> FEATURE:
<223> OTHER INFORMATION: HER-2/neu-650

<400> SEQUENCE: 52

Pro Leu Thr Ser Ile Ile Ser Ala Val
1               5

<210> SEQ ID NO 53
<211> LENGTH: 9
<212> TYPE: PRT
<213> ORGANISM: Artificial
<220> FEATURE:
<223> OTHER INFORMATION: HER-2/neu-650Y1

<400> SEQUENCE: 53

Tyr Leu Thr Ser Ile Ile Ser Ala Val
1               5

<210> SEQ ID NO 54
<211> LENGTH: 9
<212> TYPE: PRT
<213> ORGANISM: Artificial
<220> FEATURE:
<223> OTHER INFORMATION: HER-2/neu-466

<400> SEQUENCE: 54

Ala Leu Ile His His Asn Thr His Leu
1               5

<210> SEQ ID NO 55
<211> LENGTH: 9
<212> TYPE: PRT
<213> ORGANISM: Artificial
<220> FEATURE:
<223> OTHER INFORMATION: HER-2/neu-466Y1

<400> SEQUENCE: 55

Tyr Leu Ile His His Asn Thr His Leu
1               5

<210> SEQ ID NO 56
<211> LENGTH: 9
<212> TYPE: PRT
<213> ORGANISM: Artificial
<220> FEATURE:
<223> OTHER INFORMATION: HER-2/neu-402

<400> SEQUENCE: 56

Thr Leu Glu Glu Ile Thr Gly Tyr Leu
1               5

<210> SEQ ID NO 57
<211> LENGTH: 9
<212> TYPE: PRT
<213> ORGANISM: Artificial
<220> FEATURE:
<223> OTHER INFORMATION: HER-2/neu-402Y1

<400> SEQUENCE: 57

Tyr Leu Glu Glu Ile Thr Gly Tyr Leu
1               5

<210> SEQ ID NO 58
<211> LENGTH: 9
<212> TYPE: PRT
<213> ORGANISM: Artificial
<220> FEATURE:
<223> OTHER INFORMATION: HER-2/neu-391

<400> SEQUENCE: 58

Pro Leu Gln Pro Glu Gln Leu Gln Val
1               5

<210> SEQ ID NO 59
<211> LENGTH: 9
<212> TYPE: PRT
<213> ORGANISM: Artificial
<220> FEATURE:
<223> OTHER INFORMATION: HER-2/neu-391Y1

<400> SEQUENCE: 59

Tyr Leu Gln Pro Glu Gln Leu Gln Val
1               5

<210> SEQ ID NO 60
<211> LENGTH: 9
<212> TYPE: PRT
<213> ORGANISM: Artificial
<220> FEATURE:
<223> OTHER INFORMATION: HER-2/neu-971

<400> SEQUENCE: 60

Glu Leu Val Ser Glu Phe Ser Arg Met
1               5

<210> SEQ ID NO 61
<211> LENGTH: 9
<212> TYPE: PRT
<213> ORGANISM: Artificial
<220> FEATURE:
<223> OTHER INFORMATION: HER-2/neu-971Y1

<400> SEQUENCE: 61

Tyr Leu Val Ser Glu Phe Ser Arg Met
1               5

<210> SEQ ID NO 62
<211> LENGTH: 9
<212> TYPE: PRT
<213> ORGANISM: Artificial
<220> FEATURE:
<223> OTHER INFORMATION: HBVpol-28

<400> SEQUENCE: 62

Leu Leu Asp Asp Glu Ala Gly Pro Leu
1 5

<210> SEQ ID NO 63
<211> LENGTH: 9
<212> TYPE: PRT
<213> ORGANISM: Artificial
<220> FEATURE:
<223> OTHER INFORMATION: HBVpol-28Y1

<400> SEQUENCE: 63

Tyr Leu Asp Asp Glu Ala Gly Pro Leu
1 5

<210> SEQ ID NO 64
<211> LENGTH: 9
<212> TYPE: PRT
<213> ORGANISM: Artificial
<220> FEATURE:
<223> OTHER INFORMATION: HBVpol-594

<400> SEQUENCE: 64

Pro Leu Glu Glu Glu Leu Pro Arg Leu
1 5

<210> SEQ ID NO 65
<211> LENGTH: 9
<212> TYPE: PRT
<213> ORGANISM: Artificial
<220> FEATURE:
<223> OTHER INFORMATION: HBVpol-594Y1

<400> SEQUENCE: 65

Tyr Leu Glu Glu Glu Leu Pro Arg Leu
1 5

<210> SEQ ID NO 66
<211> LENGTH: 9
<212> TYPE: PRT
<213> ORGANISM: Artificial
<220> FEATURE:
<223> OTHER INFORMATION: HBVpol-985

<400> SEQUENCE: 66

Asn Leu Gln Ser Leu Thr Asn Leu Leu
1 5

<210> SEQ ID NO 67
<211> LENGTH: 9
<212> TYPE: PRT
<213> ORGANISM: Artificial
<220> FEATURE:
<223> OTHER INFORMATION: HBVpol-985Y1

<400> SEQUENCE: 67

Tyr Leu Gln Ser Leu Thr Asn Leu Leu
1 5

<210> SEQ ID NO 68
<211> LENGTH: 9
<212> TYPE: PRT
<213> ORGANISM: Artificial
<220> FEATURE:
<223> OTHER INFORMATION: EphA2-61

<400> SEQUENCE: 68

Asp Met Pro Ile Tyr Met Tyr Ser Val
1 5

<210> SEQ ID NO 69
<211> LENGTH: 9
<212> TYPE: PRT
<213> ORGANISM: Artificial
<220> FEATURE:
<223> OTHER INFORMATION: EphA2-61Y1

<400> SEQUENCE: 69

Tyr Met Pro Ile Tyr Met Tyr Ser Val
1 5

<210> SEQ ID NO 70
<211> LENGTH: 10
<212> TYPE: PRT
<213> ORGANISM: Artificial
<220> FEATURE:
<223> OTHER INFORMATION: HER2-911

<400> SEQUENCE: 70

Thr Val Trp Glu Leu Met Thr Phe Gly Ala
1 5 10

<210> SEQ ID NO 71
<211> LENGTH: 10
<212> TYPE: PRT
<213> ORGANISM: Artificial
<220> FEATURE:
<223> OTHER INFORMATION: HER2-911Y1V10

<400> SEQUENCE: 71

Tyr Val Trp Glu Leu Met Thr Phe Gly Val
1 5 10

<210> SEQ ID NO 72
<211> LENGTH: 10
<212> TYPE: PRT
<213> ORGANISM: Artificial
<220> FEATURE:
<223> OTHER INFORMATION: HER4-911

<400> SEQUENCE: 72

Thr Ile Trp Glu Leu Met Thr Phe Gly Gly
1 5 10

<210> SEQ ID NO 73
<211> LENGTH: 10
<212> TYPE: PRT
<213> ORGANISM: Artificial
<220> FEATURE:
<223> OTHER INFORMATION: HER1-911

<400> SEQUENCE: 73

Thr Val Trp Glu Leu Met Thr Phe Gly Ser
1 5 10

<210> SEQ ID NO 74
<211> LENGTH: 9
<212> TYPE: PRT
<213> ORGANISM: Artificial
<220> FEATURE:
<223> OTHER INFORMATION: HER2-722

<400> SEQUENCE: 74

Lys Val Lys Val Leu Gly Ser Gly Ala
1               5

<210> SEQ ID NO 75
<211> LENGTH: 9
<212> TYPE: PRT
<213> ORGANISM: Artificial
<220> FEATURE:
<223> OTHER INFORMATION: HER2-722Y1V9

<400> SEQUENCE: 75

Tyr Val Lys Val Leu Gly Ser Gly Val
1               5

<210> SEQ ID NO 76
<211> LENGTH: 9
<212> TYPE: PRT
<213> ORGANISM: Artificial
<220> FEATURE:
<223> OTHER INFORMATION: HER3-722

<400> SEQUENCE: 76

Lys Leu Lys Val Leu Gly Ser Gly Val
1               5

<210> SEQ ID NO 77
<211> LENGTH: 9
<212> TYPE: PRT
<213> ORGANISM: Artificial
<220> FEATURE:
<223> OTHER INFORMATION: HER4-722

<400> SEQUENCE: 77

Arg Val Lys Val Leu Gly Ser Gly Ala
1               5

<210> SEQ ID NO 78
<211> LENGTH: 9
<212> TYPE: PRT
<213> ORGANISM: Artificial
<220> FEATURE:
<223> OTHER INFORMATION: HER1-722

<400> SEQUENCE: 78

Lys Ile Lys Val Leu Gly Ser Gly Ala
1               5

<210> SEQ ID NO 79
<211> LENGTH: 9
<212> TYPE: PRT
<213> ORGANISM: Artificial
<220> FEATURE:
<223> OTHER INFORMATION: HER2-845

<400> SEQUENCE: 79

Asp Leu Ala Ala Arg Asn Val Leu Val
1               5

<210> SEQ ID NO 80
<211> LENGTH: 9
<212> TYPE: PRT
<213> ORGANISM: Artificial
<220> FEATURE:
<223> OTHER INFORMATION: HER-845Y1

<400> SEQUENCE: 80

Tyr Leu Ala Ala Arg Asn Val Leu Val
1               5

<210> SEQ ID NO 81
<211> LENGTH: 9
<212> TYPE: PRT
<213> ORGANISM: Artificial
<220> FEATURE:
<223> OTHER INFORMATION: HER3-845

<400> SEQUENCE: 81

Asn Leu Ala Ala Arg Asn Val Leu Leu
1               5

<210> SEQ ID NO 82
<211> LENGTH: 9
<212> TYPE: PRT
<213> ORGANISM: Artificial
<220> FEATURE:
<223> OTHER INFORMATION: HER2-904

<400> SEQUENCE: 82

Asp Val Trp Ser Tyr Gly Val Thr Val
1               5

<210> SEQ ID NO 83
<211> LENGTH: 9
<212> TYPE: PRT
<213> ORGANISM: Artificial
<220> FEATURE:
<223> OTHER INFORMATION: HER-904Y1

<400> SEQUENCE: 83

Tyr Val Trp Ser Tyr Gly Val Thr Val
1               5

<210> SEQ ID NO 84
<211> LENGTH: 9
<212> TYPE: PRT
<213> ORGANISM: Artificial
<220> FEATURE:
<223> OTHER INFORMATION: HER4-904

<400> SEQUENCE: 84

Asp Val Trp Ser Tyr Gly Val Thr Ile
1               5

<210> SEQ ID NO 85
<211> LENGTH: 9
<212> TYPE: PRT
<213> ORGANISM: Artificial
<220> FEATURE:
<223> OTHER INFORMATION: HER2-933

<400> SEQUENCE: 85

Asp Leu Leu Glu Lys Gly Glu Arg Leu
1               5

<210> SEQ ID NO 86
<211> LENGTH: 9
<212> TYPE: PRT
<213> ORGANISM: Artificial
<220> FEATURE:
<223> OTHER INFORMATION: HER-933Y1

<400> SEQUENCE: 86

Tyr Leu Leu Glu Lys Gly Glu Arg Leu
1 5

<210> SEQ ID NO 87
<211> LENGTH: 10
<212> TYPE: PRT
<213> ORGANISM: Artificial
<220> FEATURE:
<223> OTHER INFORMATION: HER1-933

<400> SEQUENCE: 87

Ser Ile Leu Glu Leu Lys Gly Glu Arg Leu
1 5 10

<210> SEQ ID NO 88
<211> LENGTH: 10
<212> TYPE: PRT
<213> ORGANISM: Artificial
<220> FEATURE:
<223> OTHER INFORMATION: HER2-945

<400> SEQUENCE: 88

Pro Ile Cys Thr Ile Asp Val Tyr Met Ile
1 5 10

<210> SEQ ID NO 89
<211> LENGTH: 10
<212> TYPE: PRT
<213> ORGANISM: Artificial
<220> FEATURE:
<223> OTHER INFORMATION: HER3-945

<400> SEQUENCE: 89

Gln Ile Cys Thr Ile Asp Val Tyr Met Val
1 5 10

<210> SEQ ID NO 90
<211> LENGTH: 10
<212> TYPE: PRT
<213> ORGANISM: Artificial
<220> FEATURE:
<223> OTHER INFORMATION: HER-945Y1

<400> SEQUENCE: 90

Tyr Ile Cys Thr Ile Asp Val Tyr Met Val
1 5 10

<210> SEQ ID NO 91
<211> LENGTH: 10
<212> TYPE: PRT
<213> ORGANISM: Artificial
<220> FEATURE:
<223> OTHER INFORMATION: HER4-945

<400> SEQUENCE: 91

Pro Ile Cys Thr Ile Asp Val Tyr Met Val
1 5 10

<210> SEQ ID NO 92
<211> LENGTH: 10
<212> TYPE: PRT
<213> ORGANISM: Artificial
<220> FEATURE:
<223> OTHER INFORMATION: HER1-945

-continued

```
<400> SEQUENCE: 92

Pro Ile Cys Thr Ile Asp Val Tyr Lys Ile
1               5                   10
```

USE OF NATIVE PEPTIDES AND THEIR OPTIMIZED DERIVATIVES FOR VACCINATION

CROSS REFERENCE TO RELATED APPLICATIONS

Figure 1:
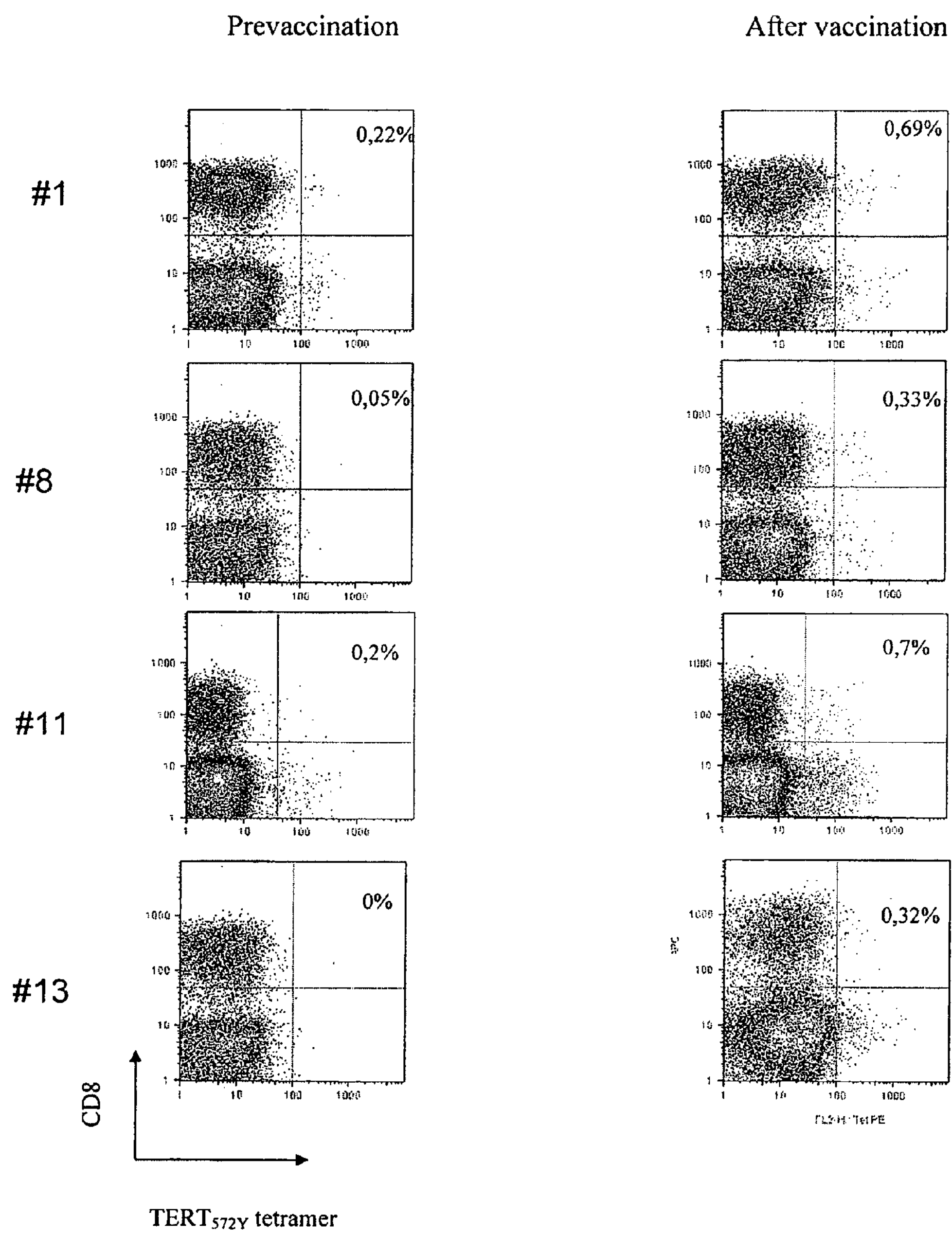

This application is a national stage application filed under 35 USC 371 of International Application No PCT/EP2006/005325, filed May 9, 2006, which claims priority from European patent Application No. 05290984.3, filed May 9, 2005.

FIELD AND BACKGROUND OF THE INVENTION

The present invention pertains to the field of vaccination, and more particularly to the fields of antitumor and antiviral vaccination. The invention concerns the use of a native peptide in a medicinal composition, for selecting and/or boosting part of a CTL immune response which has been initiated by an optimized immunogenic peptide derived from said native peptide.

Cancer immunotherapy is intended to stimulate cytotoxic T lymphocytes (CTL) recognizing peptides derived from tumor antigens and presented at the tumor cell surface by HLA class 1 molecules. CTL targeted peptides can be dominant or cryptic (Moudgil and Sercarz 1994). Dominant peptides have high HLA affinity and are frequently presented by tumor cells. In contrast, cryptic peptides have low HLA affinity and are rarely presented by tumor cells. All cancer vaccines so far tested have targeted dominant peptides, with relatively little success (Slingluff, Yamshchikov et al. 2001; Knutson, Schiffman et al. 2002; Schaed, Klimek et al. 2002; Parkhurst, Riley et al. 2004; Vonderheide, Domchek et al. 2004). Studies using mouse models showed that this lack of efficacy is due to tolerance to tumor antigens, and especially to their dominant peptides (Cibotti, Kanellopoulos et al. 1992; Theobald, Biggs et al. 1997; Colella, Bullock et al., 2000; Hernandez, Lee et al. 2000; Grossmann, Davila et al. 2001; Gross, Graff-Dubois et al. 2004).

To circumvent this tolerance, vaccination with cryptic peptides was recently proposed. It was observed that in humanized mice, tolerance of cryptic peptides was weak or absent, and that cryptic peptides efficiently induced antitumoral immunity in vivo, providing their immunogenicity had been optimized (Tourdot, Scardino et al. 2000; Scardino, Gross et al. 2002; Gross, Graff-Dubois et al. 2004). A peptide sequence modification that optimizes immunogenicity of almost all low-affinity HLA-A*0201-restricted peptides tested was previously described (Tourdot, Scardino et al. 2000).

$TERT_{572Y}$ is an HLA-A*0201-associated optimized cryptic peptide derived from TERT, an antigen overexpressed by 85% of human tumors (Kim, Piatyszek et al. 1994). $TERT_{572}$ is present in both human and murine TERT, and $TERT_{572Y}$ was able to induce antitumoral immunity in HLA-A*0201 transgenic mice, however no autoimmunity against normal TERT-expressing tissues was observed (Gross, Graff-Dubois et al. 2004). In vitro, $TERT_{572Y}$ stimulated antitumor CTLs from both healthy donors and prostate cancer patients. CTLs killed TERT-expressing tumor cells but not TERT-expressing normal cells (Hernandez, Garcia-Pons et al. 2002; Scardino, Gross et al. 2002).

However, in a similar vaccination approach, it has been reported that vaccination of melanoma patients with optimized $gp100_{209M}$ led to the amplification of T cells that were no longer able to recognize either the native $gp100_{209}$ peptide or gp100-expressing melanoma cells (Clay, Custer et al. 1999).

SUMMARY OF THE INVENTION

Hence, there is presently a need for a vaccination protocol which enables the initiation and maintenance of a T cell response targeting sub-dominant or cryptic epitopes, especially when this response is initiated by optimized peptides.

The study disclosed in Example 1 below was designed to evaluate: i) the capacity of $TERT_{572Y}$ to stimulate an antitumor immune response in vivo in patients with advanced cancer; and ii) the risk of inducing autoimmunity against TERT-expressing normal cells and tissues such as hematopoietic precursors, gut, thymus and liver. Vaccination of advanced cancer patients with $TERT_{572Y}$ stimulated specific CTLs that were fully functional and able to kill in vitro tumor cells overexpressing TERT. Moreover, vaccination was safe and did not induce any autoimmunity against TERT positive normal tissues. This is the first in vivo demonstration in humans that optimized cryptic peptides can be considered for tumor immunotherapy.

Moreover, these results, as well as those presented in Examples 2, 3 and 4, show that injection of a native peptide, following vaccination with its cognate optimized peptide, can maintain the immune response initiated by said optimized peptide. Without being bound by theory, it can be hypothesized that the use of the native peptide allows to select and/or boost, among T cells recruited by the optimized peptide, those with the highest specificity for the native peptide presented by tumor cells.

These findings allow to propose the use of a native cryptic or non-optimized peptide for improving the CTL immune response raised by a cognate optimized peptide.

A "cryptic peptide" for a given MHC molecule is a peptide which is capable to bind said MHC molecule, but only with a weak affinity for the MHC molecule and/or a weak stability of the MHC/peptide complex. As a result this peptide is only poorly presented by said MHC molecule at the surface of an antigen presenting cell, and thus participate only slightly, or not at all, in the CTL response to the antigen from which said peptide is derived. For example, in the case of HLA A2, cryptic peptides can be defined as peptides which have a low affinity and a weak stabilizing ability ($RA>5$ and $DC_{50}<2$ hours), as described in WO 0208716.

A "native peptide" (cryptic or not) is a peptide which corresponds to a fragment of an antigen, without any sequence modification.

An "optimized peptide" for a given native peptide is a peptide obtained by one or several amino acid substitutions in said native peptide, said modifications resulting in a greater affinity for the MHC molecule and/or a greater stability of the MHC/peptide complex. For example, HLA-A2.1-associated peptides can be optimized by modifying their sequence by introducing a tyrosine in the first position (P1Y substitution) (Tourdot, Scardino et al. 2000). A method for identifying cryptic peptides and generating cognate optimized peptides is disclosed for instance in PCT WO 02/08716, the content of which is incorporated herein by reference. Other modifications for optimizing HLA A2 peptides have also been described, such as substituting the amino acid in position 2 by a methionine or a leucine (Parkhurst, Salgaller et al., 1996; Bakker, van der Burg et al., 1997; Valmori, Fonteneau et al., 1998), or substituting the C-terminal amino acid by a valine or a leucine (Parkhurst, Salgaller et al., 1996). These peptide modifications can be done to obtain optimized peptides to perform the present invention.

A cryptic peptide is not able to generate in vitro a specific CTL response against target cells expressing the protein from which it is derived. In contrast, the cognate optimized peptide is able to generate a specific CTL response against the same target cells, wherein at least part of the CTLs have a high avidity for said cryptic peptide.

An object of the present invention is the use of a native peptide, for producing a medicinal composition for maintaining the CTL immune response initiated by its cognate optimized peptide. According a preferred embodiment of the invention, the native peptide is sub-dominant or cryptic.

The present invention is particularly useful in the domain of antitumor or antiviral immunotherapy. Accordingly, the native peptide is advantageously from a tumor antigen or from a viral antigen, especially from an antigen from a virus which produces long-lasting infections, such as HIV, HCV and HBV.

According to the invention, a native peptide can be used for vaccination of patients having previously received a cognate optimized peptide.

The present invention thus encompasses a method for vaccinating a patient against a tumoral or viral antigen, wherein said method comprises a first step of vaccination with an optimized peptide cognate to a native peptide of said antigen, particularly a cryptic peptide, followed by a second step of vaccination with said native peptide.

An example of antitumoral vaccination using the native cryptic peptide TERT572 (RLFFYRKSV) (SEQ ID NO: 1) and its cognate optimized peptide TERT572Y (YLFFYRKSV) (SEQ ID NO:2), is given hereinafter in Example 1.

According to a preferred embodiment of the invention, the cryptic peptide is presented by HLA A2, and the optimized peptide results from the substitution of the N-terminal amino acid of said cryptic peptide with a tyrosine residue. Non-limitative examples of couples of cryptic peptides and optimized peptides, presented by HLA A2, and which can be used in the present invention are described in PCT WO 02/08716 and in Table 1 below. Other couples of native and cognate optimized peptides which can be used according to the present invention, are also presented in Table 1.

TABLE 1 examples of couples of native and optimized peptides, presented by HLA A2, which can be used according to the invention.

| Native peptide | | | Optimized peptide | | | |
|---|---|---|---|---|---|---|
| Name | Sequence | No | Name | Sequence | No | Reference |
| HIVgag$_{76}$ | SLYNTVATL | 13 | HIVgag$_{76Y1}$ | YLYNTVATL | 14 | WO 0208716 |
| FluM$_{58}$ | GIGLFVFTL | 11 | FluM$_{58Y1}$ | YIGLFVFTL | 12 | |
| HBVpol$_{575}$ | FLLSLGIHL | 15 | HBVpol$_{575Y1}$ | YLLSLGIHL | 16 | |
| HBVpol$_{765}$ | LLGCAANWIL | 17 | HBVpol$_{765Y1}$ | YLGCAANWIL | 18 | |
| Mart-1$_{27}$ | AAGIGILTV | 19 | Mart-1$_{27Y1}$ | YAGIGILTV | 20 | |
| Mart-1$_{26}$ | EAAGIGILTV | 21 | Mart-1$_{26L27}$ | ELAGIGILTV | 22 | Valmori, D., 1998 |
| Gp100$_{177}$ | AMLGTHTMEV | 23 | Gp100$_{177Y1}$ | YMLGTHTMEV | 24 | WO 0208716 |
| Gp100$_{178}$ | MLGTHTMEV | 25 | Gp100$_{178Y1}$ | YLGTHTMEV | 26 | |
| Gp100$_{154}$ | KTWGQYWQV | 8 | Gp100$_{154Y1}$ | YTWGQYWQV | 9 | |
| | | | Gp100$_{154M155}$ | KMWGQYWQV | 10 | Bakker, A. B., 1997 |
| Gp100$_{570}$ | SLADTNSLAV | 27 | Gp100$_{570Y1}$ | YLADTNSLAV | 28 | WO 0208716 |
| Gp100$_{209}$ | TDQVPFSV | 29 | Gp100$_{209Y1}$ | YDQVPFSV | 30 | |
| | | | Gp100$_{209M210}$ | YMQVPFSV | 31 | Parkhust, M. R., 1996 |
| Gp100$_{476}$ | VLYRYGSFSV | 32 | Gp100$_{476Y1}$ | YLYRYGSFSV | 33 | WO 0208716 |
| Gp100$_{457}$ | LLDGTATLRL | 34 | Gp100$_{457Y1}$ | YLDGTATLRL | 35 | |
| HER-2/neu$_{799}$ | QLMPYGCLL | 36 | HER-2/neu$_{799Y1}$ | YLMPYGCLL | 37 | |
| HER-2/neu$_{369}$ | KIFGSLAFL | 38 | HER-2/neu$_{369Y1}$ | YIFGSLAFL | 39 | |
| HER-2/neu$_{789}$ | CLTSTVQLV | 40 | HER-2/neu$_{789Y1}$ | YLTSTVQLV | 41 | |
| HER-2/neu$_{48}$ | HLYQGCQW | 42 | HER-2/neu$_{48Y1}$ | YLYQGCQW | 43 | |
| HER-2/neu$_{773}$ | VMAGVGSPYV | 44 | HER-2/neu$_{773Y1}$ | YMAGVGSPYV | 45 | |
| HER-2/neu$_{5}$ | ALCRWGLL | 46 | HER-2/neu$_{5Y1}$ | YLCRWGLL | 47 | |
| HER-2/neu$_{851}$ | VLVKSPNHV | 48 | HER-2/neu$_{851Y1}$ | YLVKSPNHV | 49 | |
| HER-2/neu$_{661}$ | ILLVVVLGV | 50 | HER-2/neu$_{661Y1}$ | YLLVVVLGV | 51 | |
| HER-2/neu$_{650}$ | PLTSIISAV | 52 | HER-2/neu$_{650Y1}$ | YLTSIISAV | 53 | |
| HER-2/neu$_{466}$ | ALIHHNTHL | 54 | HER-2/neu$_{466Y1}$ | YLIHHNTHL | 55 | |
| HER-2/neu$_{402}$ | TLEEITGYL | 56 | HER-2/neu$_{402Y1}$ | YLEEITGYL | 57 | |
| HER-2/neu$_{391}$ | PLQPEQLQV | 58 | HER-2/neu$_{391Y1}$ | YLQPEQLQV | 59 | |
| HER-2/neu$_{971}$ | ELVSEFSRM | 60 | HER-2/neu$_{971Y1}$ | YLVSEFSRM | 61 | |
| HBVpol$_{28}$ | LLDDEAGPL | 62 | HBVpol$_{28Y1}$ | YLDDEAGPL | 63 | |
| HBVpol$_{594}$ | PLEEELPRL | 64 | HBVpol$_{594Y1}$ | YLEEELPRL | 65 | |
| HBVpol$_{985}$ | NLQSLTNLL | 66 | HBVpol$_{985Y1}$ | YLQSLTNLL | 67 | |
| EphA2$_{61}$ | DMPIYMYSV | 68 | EphA2$_{61Y1}$ | YMPIYMYSV | 69 | WO 03091383 |
| HER2$_{911}$ | TVWELMTFGA | 70 | HER$_{911Y1V10}$ | YVWELMTFGV | 71 | WO 03083124 |
| HER4$_{911}$ | TIWELMTFGG | 72 | | | | |
| HER1$_{911}$ | TVWELMTFGS | 73 | | | | |
| HER2$_{722}$ | KVKVLGSGA | 74 | HER$_{722Y1V9}$ | YVKVLGSGV | 75 | |
| HER3$_{722}$ | KLKVLGSGV | 76 | | | | |
| HER4$_{722}$ | RVKVLGSGA | 77 | | | | |
| HER1$_{722}$ | KIKVLGSGA | 78 | | | | |
| HER2$_{845}$ | DLAARNVLV | 79 | HER$_{845Y1}$ | YLAARNVLV | 80 | |
| HER3$_{845}$ | NLAARNVLL | 81 | | | | |
| HER2$_{904}$ | DVWSYGVTV | 82 | HER$_{904Y1}$ | YVWSYGVTV | 83 | |
| HER4$_{904}$ | DVWSYGVTI | 84 | | | | |
| HER2$_{933}$ | DLLEKGERL | 85 | HER$_{933Y1}$ | YLLEKGERL | 86 | |
| HER1$_{933}$ | SILELKGERL | 87 | | | | |

TABLE 1-continued examples of couples of native and optimized peptides, presented by HLA A2, which can be used according to the invention.

| Native peptide | | | Optimized peptide | | | |
|---|---|---|---|---|---|---|
| Name | Sequence | No | Name | Sequence | No | Reference |
| $HER2_{945}$ | PICTIDVYMI | 88 | $HER_{945Y1}$ | YICTIDVYMV | 90 | |
| $HER3_{945}$ | QICTIDVYMV | 89 | | | | |
| $HER4_{945}$ | PICTIDVYMV | 91 | | | | |
| $HER1_{945}$ | PICTIDVYKI | 92 | | | | |
| MAGE-$A_{248G9}$ | YLEYRQVPG | 7 | MAGE-$A_{248V9}$ | YLEYRQVPV | 6 | |
| MAGE-$A_{248D9}$ | YLEYRQVPD | 5 | | | | |
| $TERT_{988}$ | DLQVNSLQTV | 3 | $TERT_{988Y1}$ | YLQVNSLQTV | 4 | WO 0208716 |
| $TERT_{572}$ | RLFFYRKSV | 1 | $TERT_{572Y1}$ | YLFFYRKSV | 2 | |

Another aspect of the present invention is a process for in vitro obtaining CTLs having high avidity for a native peptide, especially a native cryptic peptide, by stimulating, with said native peptide, the CTLs which are present in a biological sample from a patient who has been immunized with a cognate optimized peptide. In this process, the native and optimized peptides are advantageously as described above.

The present invention also pertains to a kit of parts for the vaccination, comprising at least one dose of a native peptide and at least one dose of its cognate optimized peptide. In a preferred embodiment, the vaccination kit comprises 2 or 3 doses of optimized peptide, and 3, 4, 5 or 6 doses of native peptide. A particular vaccination kit according to the invention is adapted for the first vaccination sequence of 6 injections, and comprises 2 or 3 doses of optimized peptide, and 4 or 3 doses of native peptide. In case of long-lasting diseases, it is preferable to maintain the level of immunity obtained after this primo-vaccination, by regular recalls. This can be done, for example, by injections performed every 3 to 6 months. Therefore, complementary kits, comprising at least 2 doses, and up to 40 or 50 doses of native peptide, are also part of the present invention. Alternatively, the vaccination kit can comprise 2 to 3 doses of optimized peptide, and 3 to 40 or up to 50 doses of native peptide. Of course, said native and optimized peptides present in the kit are as described above.

Each dose comprises between 0.5 and 10 mg of peptide, preferably from 1 to 5 mg. In a preferred embodiment, each dose is formulated for subcutaneous injection. For example, each dose can be formulated in 0.3 to 1.5 ml of an emulsion of aqueous solution emulsified with Montanide, used as an adjuvant. The skilled artisan can choose any other adjuvant(s) in place of (or in addition to) Montanide. In a particular embodiment, the doses are in the form of an aqueous solution. Alternatively, the doses can be in the form of a lyophilized peptide, for extemporaneous preparation of the liquid solution to be injected.

The invention is further illustrated by the following figures and examples.

LEGENDS OF FIGURES

FIG. 1: $TERT_{572Y}$-specific CD8 cells detected ex vivo in patients #1, #3, #8, #11 and #13. Thawed PBMC from patients #1, #8, #11 and #13 collected before vaccination and after the second (#1, #8, #11) and sixth (#13) vaccine injections were stained with PE-labeled $TERT_{572Y}$ tetramer, APC-labeled anti-CD8 and FITC-labeled anti-CD3. CD3+ gated cells were analyzed.

Figure 2:
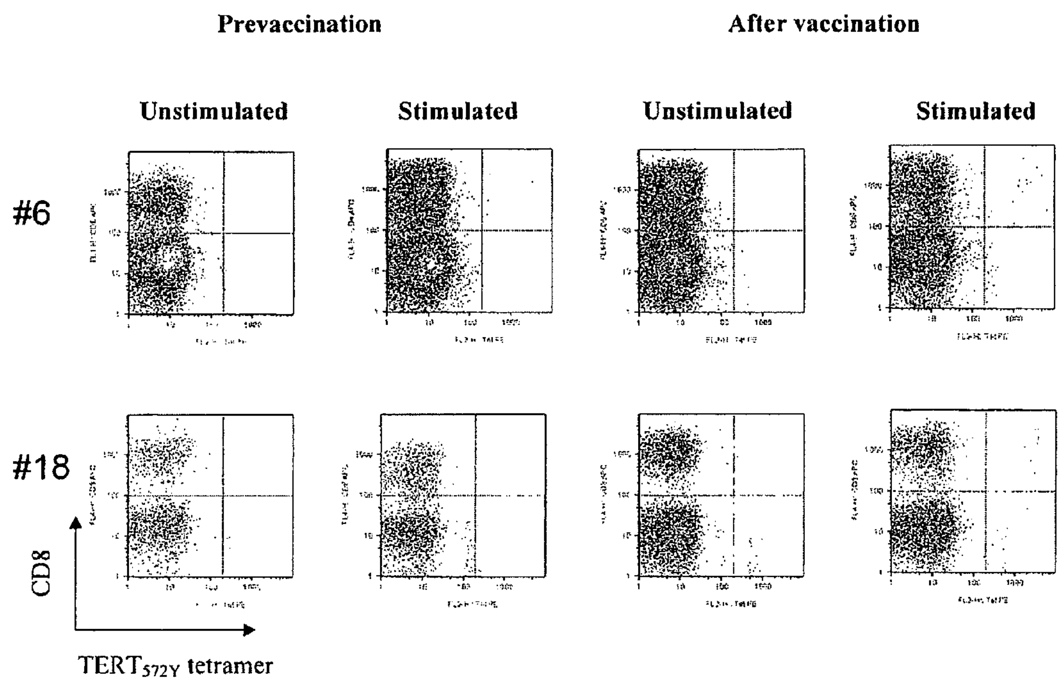

FIG. 2: $TERT_{572Y}$-specific CD8 cells detected after in vitro stimulation of PBMC from patients #6 and #18. Thawed PBMC from patients #6 and #18 were cultured in the absence (unstimulated) or presence (stimulated) of 10 μM $TERT_{572Y}$ for nine days. Cells were then stained and analyzed as described in the legend of FIG. 1.

Figure 3:
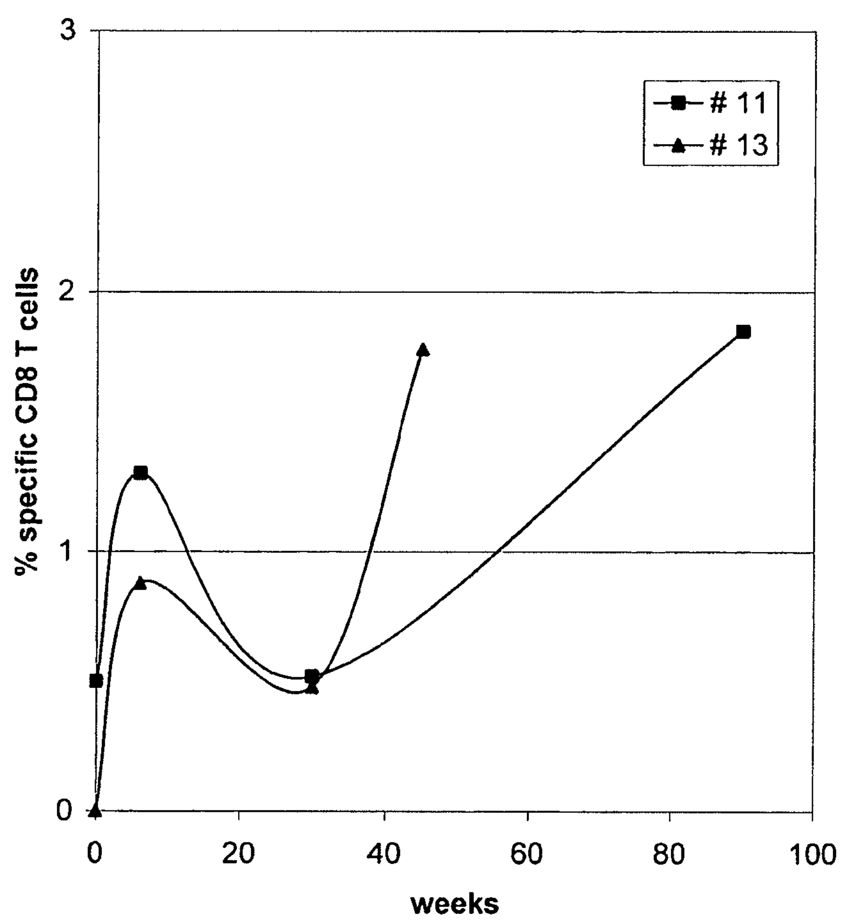

FIG. 3: Time course of immune responses.

Figure 4:
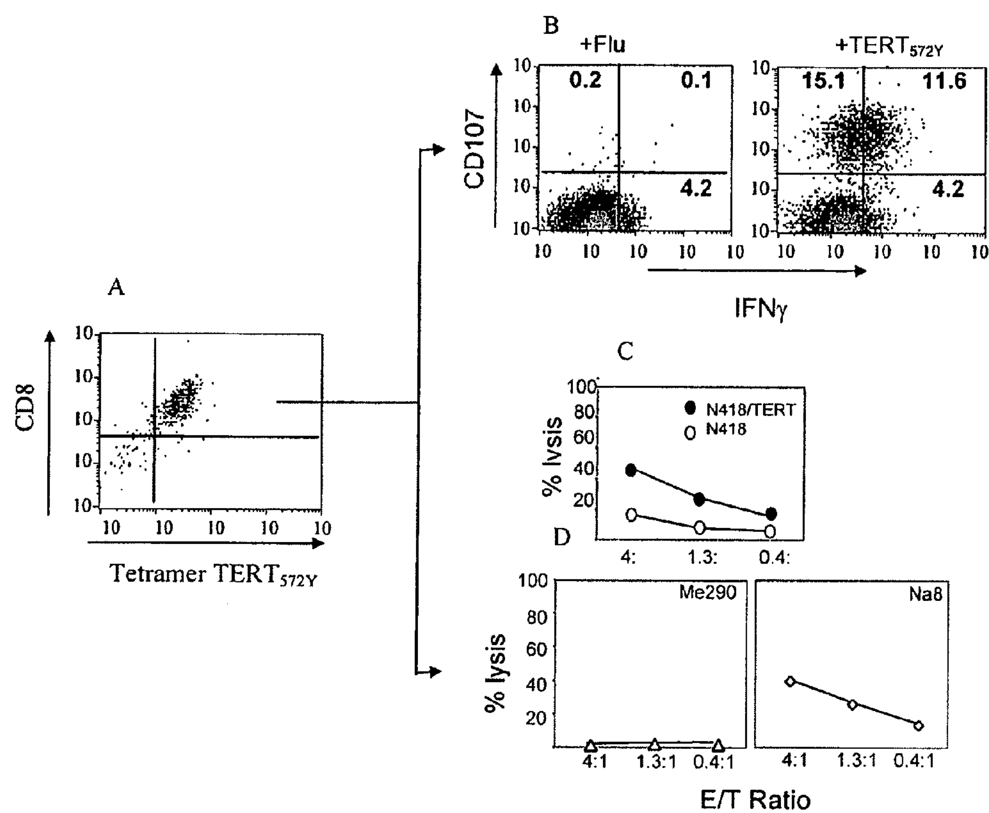

FIG. 4: Functional analysis of $TERT_{572Y}$-specific CD8 cells induced by vaccination A) PBMC from patient #4, collected three weeks after the second vaccine injection, were stimulated in vitro with $TERT_{572Y}$ peptide for nine days. $TERT_{572Y}$ specific cells were purified and amplified with PHA. Amplified cells were stained with $TERT_{572Y}$ tetramer and CD8 mAb.

B) $TERT_{572Y}$ tetramer-positive cells were stimulated with $TERT_{572Y}$ and irrelevant FluM58 peptides for 6 hours, then stained with PE-labeled anti-CD107a, permeabilized with Saponin and stained with FITC-labeled anti-IFNγ to evaluate intracellular IFNγ.

C) $TERT_{572Y}$ tetramer-positive cells were incubated with $^{51}$Cr-labeled N418 and TERT-transfected N418 cells for four hours in a classical $^{51}$Cr release assay. E/T ratios are indicated.

D) $TERT_{572Y}$ tetramer-positive cells were incubated with $^{51}$Cr-labeled NA8 and ME290 tumor cells for four hours in a classical $^{51}$Cr release assay. E/T ratios are indicated.

EXAMPLES

Example 1

Safety and Immunogenicity of the Optimized Cryptic Peptide $TERT_{572Y}$ in Patients with Advanced Malignancies

Phase I Clinical Study 1.1. Patients and Methods

Patients

Patients with chemotherapy-resistant malignant tumors were eligible for the study. Other eligibility criteria were: progressive disease for which there was no other therapeutic option of proven benefit; an expected survival of at least 6 months; patients had to be HLA-A*0201 positive; age 18-75 years old, performance status (WHO)<2, adequate bone marrow (absolute neutrophil count≥1500/mm$^3$; absolute lymphocyte count≥1300/mm$^3$; platelets>100000/mm$^3$; Hgb>10 g/dl), renal (creatinine<1.5 mg/dl) and liver (bilirubin<1.5 times the upper normal value) function. Patients were excluded if they had received chemotherapy, radiotherapy, hormonotherapy, immunotherapy or corticosteroids within one month before enrolment or if they had a known immunodeficiency or autoimmune disease. The protocol had been approved by the Ethics and Scientific Committees of the University Hospital of Heraklion and the National Drug Administration of Greece. All patients gave written informed consent in order to participate in the study.

Peptide Vaccine Preparation

The vaccine consisted of optimized TERT572Y (YLFFYRKSV) (SEQ ID NO:2) and native TERT572 (RLFFYRKSV) (SEQ ID NO:1) peptides emulsified in Montanide ISA51 (Seppic Inc, France). The vaccine peptides were synthesized at the Faculty of Pharmacy, University of Patras (Greece) by means of solid-phase Fmoc/Bu chemistry. Quality assurance studies included confirmation of identity, sterility and purity (>95% for both peptides). No decrease in purity or concentration was observed after more than two years of storage at −80° C. Each peptide was prepared as a lyophilized powder for reconstitution and dilution in sterile water.

Vaccination Protocol

Patients received a total of six subcutaneous vaccinations administered every 3 weeks. Peptides in 0.5 ml aqueous solution were emulsified with 0.5 ml Montanide ISA51 immediately before being injected. The optimized $TERT_{572Y}$ peptide was used for the first 2 vaccinations and the native $TERT_{572}$ peptide for the remaining 4 vaccinations. Five dose levels of the peptides were studied; dose levels included 2, 3, 4, 5 and 6 mg of both peptides. Three patients were entered at each dose level. An additional 3 patients were planned to be enrolled at the dose level where a dose-limiting event was observed. Each patient received the same peptide dose for all six vaccinations. No other treatment with possible antitumor activity, i.e., chemotherapy, radiotherapy, hormonal therapy or administration of corticosteroids, was allowed during the course of vaccination.

Patient Evaluation

Before entering the study, all patients were assessed by complete medical history, physical examination, and complete blood cell count with differential, serum chemistry and baseline measurements of relevant tumor markers. Moreover, measurable disease was determined by standard imaging procedures (chest x-ray, ultrasound, computed tomography scans of thorax and abdomen, magnetic resonance imaging (MRI) if indicated, and whole body bone scans). Toxicity during the vaccination protocol was evaluated by repeating the complete blood cell count weekly and by performing medical history, physical examination and serum chemistry every three weeks before each subsequent injection during the vaccination period and every month thereafter during the follow up. Toxicity was assessed and scored using the National Cancer Institute (NCI) Common Toxicity Criteria (Ajani, Welch et al. 1990). Dose-limiting toxicity (DLT) was assessed during the entire vaccination protocol and was defined as the occurrence of any of the following: grade 4 hematologic toxicity; grade 3-4 neutropenia with fever>38.2° C.; grade 3-4 non-hematologic toxicity; and any treatment delay because of toxicity. Dose escalation was discontinued and the DLT dose level was reached if at least 50% of the patients treated at that level develop a DLT. The MTD dose level was defined as the first level below the DLT dose level.

Response to treatment was evaluated by repeating the baseline imaging studies and relevant tumor marker measurements after every 2 vaccinations or sooner if clinically indicated. Response to treatment was scored as complete response (CR), partial response (PR), stable disease (SD) and progressive disease (PD) using the standard WHO criteria (Miller, Hoogstraten et al. 1981). Radiological responses were confirmed by an independent panel of radiologists. CR and PR had to be maintained for a minimum of 4 weeks. The duration of response was measured from the first documentation of response to disease progression. Time to progression (TTP) was determined by the interval between the initiation of therapy to the first date that disease progression was objectively documented. Overall survival (OS) was measured from the date of study entry to the date of death. The follow up time was measured from the day of first treatment administration to last contact or death. Immune responses were examined before the first injection, and after the second, fourth and sixth injections. Peripheral blood mononuclear cells (PBMC) were collected at each time point and frozen.

Cell Lines

T2 is a mutant human T/B hybrid that lacks TAP molecules but expresses HLA-A*0201. HLA-A*0201-positive N418 fibroblasts, TERT-transfected N418 cells and the melanoma cell lines Na8 and Me290 were provided by P. Romero (Ludwig Institute for Cancer Research, Lausanne, Switzerland).

Peptides

Class I-restricted peptides used for laboratory studies included $TERT_{572}$ (RLFFYRKSV, SEQ ID No: 1), $TERT_{572Y}$ (YLFFYRKSV, SEQ ID No: 2), and $FluM_{58}$ (GILGFVFTL, SEQ ID No: 11), all produced by Epytop (Nimes, France).

In Vitro Stimulation of PBMC

Thawed PBMC ($3\times10^5$ cells/well in 200 μl) were incubated in the presence of 10 μM $TERT_{572Y}$ peptide in complete medium (RPMI 1640 supplemented with 8% human AB serum) in 96-well round-bottom plates. IL2 was added at a final concentration of 10 U/ml after 48 h and 96 h. Cells were incubated at 37° C. in 5% $CO_2$-air. On day 9 of culture, cells from six wells were pooled and analyzed for the presence of $TERT_{572Y}$-specific CD8 cells by $TERT_{572Y}$ tetramer staining.

$TERT_{572Y}$ Tetramer Staining

Cells were incubated with PE-conjugated $TERT_{572Y}$ tetramer (Proimmune Ltd, Oxford, UK) for 30 min at room temperature, and then with APC-conjugated anti-CD8 (BD Pharmingen, Mississauga, Canada) and FITC-conjugated anti-CD3 (BD Pharmingen, Mississauga, Canada) mAbs for 30 min at 4° C. Stained cells were analyzed by flow cytometry (FACSCalibur, BD Biosciences, Mountain View, Calif.).

Polyclonal Expansion of $TERT_{572Y}$ tetramer-positive cells

PBMCs were stimulated with 10 μM $TERT_{572Y}$ in the presence of 10 U/ml IL2 for 9 days. Cells were labeled with anti-CD8 mAb and $TERT_{572Y}$ tetramer before isolation with a cell sorter. Sorted cells were stimulated with PHA (Difco) for 14 days.

CD107 and Intracellular IFNγ Double Labeling

T cells were stimulated with T2 cells loaded with peptide (10 μM) in the presence of 20 μg/ml Brefeldin A (Sigma, Oakville, Canada). Six hours later they were washed, stained with PE-conjugated anti-CD107 mAb (BD Pharmingen, Mississauga, Canada) in PBS for 25 minutes at 4° C., washed again and fixed with 4% paraformaldehyde. The cells were permeabilized with PBS/0.2% Saponin/0.5% BSA (Sigma) and stained with APC-conjugated anti-IFNγ mAb (BD Pharmingen, Mississauga, Canada) before flow cytometric analysis (FACSCalibur, BD Biosciences, Mountain View, Calif.).

Cytotoxicity Assay

Target cells were labeled with 100 μCi of $^{51}Cr$ for 90 min, washed twice, and plated in 96-well round-bottom plates ($3\times10^3$ cells/well in 100 μl of RPMI 1640 plus 5% fetal calf serum). Effectors cells (100 μl) were then added to each well. After 4 h, 100 μl of supernatant was collected and radioactivity was measured with a gamma counter. The percentage of specific lysis was determined as follows: lysis=(experimental release-spontaneous release)/(maximum release-spontaneous release)×100.

1.2. Results

Patient Characteristics, Vaccination, and Clinical Responses

The characteristics of the 19 patients enrolled in the trial are shown in Table 2. All but one patient (patient #11) had stage 1V cancer with multiple metastases mainly in the bones, liver and lung. They all had active and progressive disease and had received several treatments, mainly chemotherapy, before entering the vaccination protocol. Three patients were enrolled at dose levels 2, 3, 4 and 5 mg of the peptides, while seven patients received the 6 mg dose. Five patients were withdrawn from the protocol after the fourth (#1, #5, #14 and #19) or fifth (#18) vaccine injection because of rapid disease progression. All five patients subsequently died within six months of disease progression. The remaining 14 patients completed the vaccination protocol. The disease stabilized in four (29%) patients (#9, #11, #12 and #13) and continued to progress in 10 patients. The latter 10 patients subsequently received chemotherapy, and six of them are still alive. One (patient #11) of the 4 patients whose disease stabilized for 9 months subsequently progressed, while the other three patients still have stable disease (after 12 months for patients #9 and #12, and 9 months for patient #13) with no additional therapy after the end of vaccination.

Overall, after a median follow up of 10.7 months (range 4.4-27.6), nine patients have died, all due to disease progression. The median time to tumor progression was 4.2 months (range 2.3-11.2) and the median overall survival 15.2 months (range 4.4-27.6).

Toxicity and Adverse Events

No DLT was observed throughout the entire study and therefore the MTD dose level has not been reached (Table 3). Thirteen patients developed grade I toxicity. It consisted of local skin reaction (11 patients), anemia (6 patients), thrombocytopenia (2 patients), fatigue (1 patient) and anorexia (1 patient). Except of local skin reaction, other toxicities were most likely related to the disease rather than the vaccination. Grade I toxicities appeared early in the vaccination course. Three patients developed grade 11 toxicity consisting of fatigue (3 patients), nausea (2 patients) and anorexia (2 patients). In patient #5 (NSCLC) fatigue and nausea appeared after the third vaccination and disappeared two weeks later without any specific treatment. In patient #10 (colorectal cancer) fatigue, nausea and anorexia observed after the third vaccination were felt to be due to the disease rather than the vaccination. This patient developed a fatal intestinal obstruction. Patient #18 had an extremely rapid progression of her

TABLE 2

Patient characteristics.

| Pt | Age | Sex | Cancer | Stage | PS | Previous treatment | Dose of vaccine | No of injections | Clinical response | Survival (months) |
|---|---|---|---|---|---|---|---|---|---|---|
| #1 | 73 | M | colorectal | IV | 1 | 7 lines CT | 2 mg | 4 | PD | 6.1 |
| #2 | 75 | F | breast | IV | 1 | 5 lines CT | 2 mg | 6 | PD | 27.6 |
| #3 | 64 | M | melanoma | IV | 1 | 1 line CT | 2 mg | 6 | PD | 8.8+ |
| #4 | 60 | M | NSCLC | IV | 1 | 2 lines CT | 3 mg | 6 | PD | 22.8+ |
| #5 | 71 | M | NSCLC | IV | 1 | 6 lines CT | 3 mg | 4 | PD | 5.7 |
| #6 | 73 | F | cervix | IV | 1 | 2 lines CT | 3 mg | 6 | PD | 5.3 |
| #7 | 53 | M | head and neck | IV | 1 | 4 lines CT | 4 mg | 6 | PD | 15.1 |
| #8 | 57 | F | colorectal | IV | 1 | 5 lines CT | 4 mg | 6 | PD | 12.3 |
| #9 | 66 | M | renal | IV | 1 | 1 line IT | 4 mg | 6 | SD | 11.1+ |
| #10 | 73 | F | colorectal | IV | 1 | 2 lines CT | 5 mg | 6 | PD | 4.6 |
| #11 | 49 | M | NSCLC | IIIb | 0 | 3 lines CT | 5 mg | 6 | SD | 17.5+ |
| #12 | 45 | F | breast | IV | 1 | 2 lines CT | 5 mg | 6 | SD | 11.2+ |
| #13 | 51 | M | renal | IV | 1 | 1 line CT, 1 line IT | 6 mg | 6 | SD | 6.9+ |
| #14 | 61 | M | unknown origin | IV | 1 | 2 lines CT | 6 mg | 4 | PD | 8 |
| #15 | 70 | F | colorectal | IV | 0 | 2 lines CT | 6 mg | 6 | PD | 10.7+ |
| #16 | 69 | M | prostate | IV | 1 | 2 lines CT 1 line HT | 6 mg | 6 | PD | 17+ |
| #17 | 69 | F | ovarian | IV | 1 | 8 lines CT | 6 mg | 6 | PD | 13.7+ |
| #18 | 51 | F | ovarian | IV | 1 | 4 lines CT | 6 mg | 5 | PD | 6.4 |
| #19 | 48 | M | esophagus | IV | 1 | 1 line CT | 6 mg | 4 | PD | 4.4+ |

NSCLC = non small cell lung cancer,
S = surgery,
CT = chemotherapy,
HT = hormone therapy,
RT = radiotherapy,
IT = immunotherapy (IL2, INFα),
PS = performance status,
PD = progressive disease,
SD = stable disease disease and consequently was taken off the protocol after the fourth vaccination. She died two months later. Specifically, no significant hematologic, renal, gastrointestinal or hepatic toxicity was observed although TERT is expressed in these normal cells and tissues. Patients were monitored for toxicity for a median of 10.7 months (range 4.4-27.6). Even after completing or discontinuing the vaccination program patients were followed monthly for the occurrence of any delayed toxicity. However, no signs or findings of delayed toxicity were observed.

TABLE 3

Toxicity

| Patient | Toxicity Grade I | Grade II | Grade III/IV |
|---|---|---|---|
| #1 | no | no | no |
| #2 | Local skin | no | no |
| #3 | Anemia, local skin | no | no |
| #4 | Local skin | no | no |
| #5 | no | fatigue, nausea | no |
| #6 | Anemia, local skin, fatigue, anorexia | no | no |
| #7 | no | no | no |
| #8 | Thrombo/penia, local skin | no | no |
| #9 | Local skin | no | no |
| #10 | no | anorexia, fatigue, nausea | no |
| #11 | thrombocytopenia | no | no |
| #12 | Anemia, local skin | no | no |
| #13 | Local skin | no | no |
| #14 | Local skin | no | no |
| #15 | no | no | no |

TABLE 3-continued

Toxicity

| Patient | Toxicity Grade I | Grade II | Grade III/IV |
|---|---|---|---|
| #16 | Anemia | no | no |
| #17 | Anemia, local skin | no | no |
| #18 | Local skin, anemia | anorexia, fatigue | no |
| #19 | no | no | no |

Immune Responses

Peptide-specific $CD8^+$ cells were detected in peripheral blood by triple staining of PBMCs with $TERT_{572Y}$ tetramer, anti-CD8 and anti-CD3 mAbs, both ex vivo and after 9 days of stimulation in vitro with $TERT_{572Y}$ peptide. In a preliminary study, $TERT_{572Y}$ tetramer labeled less than 0.1% of CD8 cells in seven HLA-A*0201 healthy donors (mean 0.035±0.035, range 0.0-0.11%) (data not shown). The positivity cutoff for specific immunity was therefore set at 0.14% (mean ±3SD). Immune responses were studied in 14 vaccinated patients (Table 4). Only one patient (#2) failed to respond to the vaccine. $TERT_{572Y}$-specific cells were detected ex vivo in four (29%) patients (FIG. 1). Specific immunity appeared after the second injection in patients #1, #8 and #11, and after the sixth vaccination in patient #13. It is noteworthy that, prior to vaccination, $TERT_{572Y}$ tetramer labeled 0.29%, 0.33% and 1.00% of $CD8^+$ cells in patients #1, #8 and #11 after in vitro PBMC stimulation (Table 4). $TERT_{572Y}$-specific cells were also detected in 9 patients (64%) after in vitro stimulation, 3 weeks after the $2^{nd}$ (#3, #4, #5, #6, #12, #15, and #19) or the $4^{th}$ (#7 and #18) injection. Representative results (patients #6 and #18) are shown in FIG. 2. Immune response was also measured 3 and 14 months after the end of the vaccination protocol in patients #13 and #11 respectively. In all two patients more than 1.5% of tetramer positive CD8 cells were detected after in vitro stimulation of their PBMC (FIG. 3).

TABLE 4

Percentage of tetramer $TERT_{572Y}$-positive CD8 cells among peripheral blood mononuclear cells of vaccinated patients. % above background in bold

| Patient | Pre-vaccination unstimulated | Pre-vaccination stimulated | After the $2^{nd}$ or $4^{th}$ injection unstimulated | After the $2^{nd}$ or $4^{th}$ injection stimulated | Post-vaccination unstimulated | Post-vaccination stimulated |
|---|---|---|---|---|---|---|
| #1 | 0.14 | **0.29** | **0.69** | **1.25** | NT | NT |
| #2 | 0.02 | 0 | 0 | 0.11 | NT | NT |
| #3 | 0 | 0 | 0.11 | **1.14** | NT | NT |
| #4 | NT | NT | 0.05 | **4.00** | 0.02 | **0.48** |
| #5 | 0.01 | 0 | 0.06 | **0.36** | NT | NT |
| #6 | 0 | 0.01 | 0 | **4.20** | NT | NT |
| #7 | 0.02 | 0.14 | 0.01 | **0.42** | 0.12 | **0.36** |
| #8 | 0.02 | **0.33** | **0.33** | **0.98** | NT | NT |
| #11 | **0.3** | **1.00** | **0.7** | **1.30** | 0.05 | **0.52** |
| #12 | 0.04 | 0.11 | 0.10 | **0.98** | NT | NT |
| #13 | 0 | 0 | 0 | **0.88** | **0.32** | **0.48** |
| #15 | 0 | 0.04 | 0.05 | **0.45** | NT | NT |
| #18 | 0 | 0 | 0.06 | **0.62** | NT | NT |
| #19 | 0 | 0.03 | 0 | **0.73** | NT | NT |

To assess the functionality of $TERT_{572Y}$-specific $CD8^+$ cells, $TERT_{572Y}$ tetramer-positive cells from in vitro-stimulated PBMCs from patient #4 (FIG. 4A) were sorted, amplified with PHA and tested for their capacity to specifically respond to $TERT_{572Y}$ peptide and to kill TERT-overexpressing tumor cells. More than 90% of amplified cells were labeled with $TERT_{572Y}$ tetramer (FIG. 4A). Purified $TERT_{572Y}$-specific cells were fully functional, as they produced IFNγ and showed CD107a upregulation upon activation with $TERT_{572Y}$ peptide (FIG. 4B). CTL recognized endogenous TERT and specifically killed TERT-transfected but not untransfected N418 fibroblasts (FIG. 4C). Importantly, CTLs killed tumor cells overexpressing TERT (Na8 cells) but not tumor cells expressing TERT at a low level (ME290 cells) (FIG. 4D).

1.3. Discussion

The aims of the present clinical trial were to evaluate the toxicity profile and to prove the concept that cryptic peptides derived from universal tumor antigens can induce immunity in cancer patients and can, therefore, be considered for tumor immunotherapy. The inventors used the cryptic peptide $TERT_{572}$, that is presented by HLA-A*0201 and is derived from TERT, a universal tumor antigen overexpressed by 85% of tumors. Immunogenicity had been enhanced by substituting the first amino acid by a tyrosine (Tourdot, Scardino et al. 2000). The results showed that $TERT_{572Y}$ vaccination of patients with advanced cancer stimulates specific CTLs that are fully functional and are able to kill TERT-overexpressing tumor cells in vitro. Vaccination was well tolerated and did not appear to induce autoimmunity against TERT-expressing normal tissues. These results offer the first human in vivo confirmation that optimized cryptic peptides are good candidates for tumor immunotherapy.

Tumor antigens are non mutated self proteins also expressed by normal tissues, including the thymus, and are involved in tolerance induction. Tolerance, the process by which CTL, mainly those with high-avidity, are purged from the T cell repertoire, is a major barrier hindering the development of effective antitumor T cell responses. However, tolerance mainly shapes the T cell repertoire specific for dominant rather than cryptic peptides (Cibotti, Kanellopoulos et al. 1992; Moudgil and Sercarz 1994). Using a humanized mouse model, it was recently showed that vaccination with two cryptic peptides derived from murine TERT ($TERT_{572Y}$ and $TERT_{988Y}$) recruited high-avidity CTLs capable of eliciting potent antitumoral immunity (Gross, Graff-Dubois et al. 2004). In the present clinical study, more than 90% of vaccinated patients developed specific T cells capable of killing TERT-overexpressing tumor cells. In contrast, only 50% of patients treated with the dominant peptide $TERT_{540}$ emulsified in Monatanide responded to the vaccine (Parkhurst, Riley et al. 2004). However, the natural processing of the dominant TERT540 described initially (Vonderheide, Hahn et al. 1999; Minev, Hipp et al. 2000; Vonderheide, Domchek et al. 2004) was not confirmed in more recent studies (Ayyoub, Migliaccio et al. 2001; Parkhurst, Riley et al. 2004), which suggests that possibly TERT540 does not belong to the immunological self. Given this ambiguity regarding the presentation of the dominant TERT540 peptide, a direct randomized comparison with the cryptic peptide could produce results which would be very difficult to interpret.

The vaccine response rate in the patients in the present study is higher than that obtained in the roughly fifty clinical studies of tumor vaccination reported to date (Pullarkat, Lee et al. 2003; Slingluff, Petroni et al. 2003). It is also noteworthy, that almost all previous clinical studies showing high immune response rates involved patients with minimal disease and excellent performance status (Disis, Gooley et al. 2002; Pullarkat, Lee et al. 2003; Disis, Schiffman et al. 2004; Vonderheide, Domchek et al. 2004). Scheibenbogen et al (Scheibenbogen, Lee et al. 1997) demonstrated that immune reactivity in melanoma patients correlated with disease remission. In contrast, in the present study, all patients had end-stage disease.

No correlation was found between the magnitude of the immune response and the dose of peptide administered. This is in agreement with recent data indicating that immune responses to HER2/neu vaccines did not depend on the vaccine dose (Disis, Schiffman et al. 2004). No correlation was found either between the vaccine dose and the time interval required for a detectable response to emerge. All 13 responding patients had detectable specific CTLs between the $2^{nd}$ and the $4^{th}$ vaccine injection. Rapid induction of immunity may be important in this setting, especially for patients with rapidly progressive malignancies.

The rationale for using native $TERT_{572}$ peptide for the $3^{rd}$ to the $6^{th}$ vaccine injections was to select, among T cells recruited by the optimized $TERT_{572Y}$, those with the highest specificity for $TERT_{572}$ presented by tumor cells. Indeed, Clay et al (Clay, Custer et al. 1999) have shown that vaccination of melanoma patients with optimized $gp100_{209M}$, amplified T cells that were no longer able to recognize either the native $gp100_{209}$ peptide or gp100-expressing melanoma cells. The above results show that injection of the native peptide can maintain the immune response initiated by the optimized peptide. Moreover, the persistence of the immune response more than one year after the end of vaccination suggests that native peptide presented on the surface of tumor cells can maintain the specific immune response by itself. The hallmark of antitumoral immunity in vivo is autoimmunity. Autoimmunity is acceptable when it targets non essential normal cells and tissues such as melanocytes, but may hamper vaccine development when it targets essential cells such as hematopoietic precursors. Although TERT is expressed by hematopoietic stem cells, gut, thymus, and activated B and T cells (Ramakrishnan, Eppenberger et al. 1998; Liu, Schoonmaker et al. 1999), none of the patients showed signs of autoimmunity even 24 months after the end of vaccination. This confirms previous results obtained in HLA-A*0201 transgenic HHD mice vaccinated with $TERT_{572Y}$ peptide, which is also part of murine TERT (Gross, Graff-Dubois et al. 2004). Vaccinated HHD mice developed antitumor immunity without signs of autoimmunity. Moreover, $TERT_{572Y}$-specific CTLs killed tumor cells but not activated B cells. A possible explanation is that TERT expression is insufficient on normal cells (contrary to tumor cells) to permit the presentation of low-affinity peptides like $TERT_{572}$.

The observed toxicity in the present study was essentially minimal and with the exception of transient skin reactions caused by the Montanide adjuvant, all the other mild toxicities could also be attributed to the underlying disease. Given the limitations of the small number of patients enrolled in this trial and the relatively short follow up due to the advanced disease, it can be concluded that this vaccination program is free of any major acute and short-term toxicity. However, long-term toxicities will have to be evaluated in patients with better prognosis who are more likely to be cured of their malignant disease.

For ethical reasons, this study involved patients with end-stage cancer, who are not the best candidates for tumor immunotherapy. It is now generally agreed that immunotherapy is best administered to patients with minimal residual disease, and the goal should be to prevent relapse rather than to cure advanced cancer. The inability of vaccines to eradicate actively growing tumors has been clearly shown in animals models (Cheever and Chen 1997). Although clinical antitumor activity by means of tumor shrinkage was not observed in this heavily pretreated group of patients, four patients showed long lasting disease stabilization in this phase 1 trial. These patients had previously progressive disease and developed TERT-specific CTL which could be detected in their blood even months after completing the vaccination program. It is interesting that two of these patients (#9 and #13), both with renal cell carcinoma, had been successfully treated in the past with IL2 or IFNα, confirming the sensitivity of this cancer to immunotherapy. In contrast, none of 11 patients with renal cancer who were vaccinated with the dominant $TERT_{540}$ peptide had an objective clinical response, even when they developed a peptide-specific immune response (Parkhurst, Riley et al. 2004).

In conclusion, this study demonstrates that vaccination of advanced cancer patients with the optimized cryptic $TERT_{572Y}$ peptide is safe and induces an antitumor immunity in more than 90% of patients. This is the first clinical confirmation that cryptic peptides are promising candidates for cancer immunotherapy.

Example 2

In Vitro Selection and Amplification of CTLs with a High Avidity for the Native Cryptic Peptide 2.1. Materials and Methods Peptides The peptides $TERT_{988Y}$ (YLQVNSLQTV, SEQ ID No: 4), $TERT_{988}$ (DLQVNSLQTV, SEQ ID No: 3), MAGE-$A_{248V9}$ (YLEYRQVPV, SEQ ID No: 6) and MAGE-$A_{248D9}$ (YLEYRQVPD, SEQ ID No: 5) have been produced by Epytop (Nimes, France).

Animals and Cells

The HLA-A*0201 transgenic HHD mice and the murine RMAS/HHD tumor cells were previously described (Pascolo, Bervas et al. 1997).

Generation of CTL in HHD Mice

HHD mice were injected subcutaneously with 100 μg of nonamer peptides emulsified in incomplete Freund's adjuvant (IFA) in the presence of 150 μg of the I-Ab restricted HBVcore128 T-helper epitope. Spleen cells ($5\times10^7$ cells in 10 ml) from immunized HHD mice were stimulated in vitro with peptide (10 μM) in RPMI1640+10% FCS for five days. The CTL lines were established by weekly re-stimulation in vitro with irradiated spleen cells in the presence of peptide and 50 U/ml IL-2 (Proleukin, Chiron Corp., Emeryville, Calif.).

Cytotoxic Assay

Murine RMAS/HHD cells were used as targets for cytotoxicity as described (Tourdot, Scardino et al. 2000). Briefly, $2.5\times10^3$ $^{51}$Cr-labeled targets were pulsed with increasing doses (0.00001-10 μM) of peptides at 37° C. for 60 min. Effector cells in 100 μl were then added and incubated at 37° C. for 4 hours. After incubation, 100 μl of supernatant were collected and radioactivity was measured in a gamma counter. The specific lysis was determined as:

$$\text{Lysis}=(\text{Experimental Release}-\text{Spontaneous Release})/(\text{Maximal Release}-\text{Spontaneous Release}).$$

CTL avidity is defined as the peptide concentration that gives half the maximal lysis. Hence, the lower the measured avidity (in nM), the higher the avidity of the CTLs.

In Vivo Tumor Protection Assay

HHD mice were vaccinated with 100 μg of peptide emulsified in IFA in the presence of 150 μg of the 1 Ab restricted HBVcore128 epitope once and then again two weeks later. One week after the second vaccination they were challenged subcutaneously with 2×104 EL4/HHD cells. Survival was recorded every two days.

2.2. Results

Results Obtained with a Cryptic Epitope from the TERT Antigen

HHD mice were immunized with the optimized cryptic $TERT_{988Y}$ peptide. Eleven days later, spleen cells from vaccinated mice were pooled and in vitro serially stimulated with 10 μM of either $TERT_{988Y}$ or the native cryptic $TERT_{988}$ peptides in the presence of 50 IU/ml of IL2. Stimulations were repeated every week. After the first, third and sixth in vitro stimulation, CTL lines were tested for their avidity for the native $TERT_{988}$ peptide in a classical $^{51}$Cr release cytotoxicity assay (Table 5).

TABLE 5

Avidity of CTL lines for the native $TERT_{988}$ peptide, established from $TERT_{988Y}$ primed spleen cells in vitro stimulated with either $TERT_{988Y}$ or $TERT_{988}$ peptides

| No of in vitro stimulations | Peptide used for in vitro stimulation | CTL line avidity (nM) |
|---|---|---|
| 1 | $TERT_{988}$ | 170 |
| | $TERT_{988Y}$ | 300 |
| 3 | $TERT_{988}$ | 70 |
| | $TERT_{988Y}$ | 500 |
| 6 | $TERT_{988}$ | 3 |
| | $TERT_{988Y}$ | 600 |

Results Obtained with a Cryptic Epitope from the MAGE Antigen

HHD mice were immunized with the optimized MAGE-$A_{248V9}$ peptide, corresponding to the cryptic MAGE-$A_{248D9}$ (both described in WO03083124). Eleven days later, spleen cells from vaccinated mice were pooled and in vitro serially stimulated with 100 μM of either MAGE-$A_{248V9}$ or the native cryptic MAGE-$A_{248D9}$ peptides in the presence of 50 IU/ml of IL2. Stimulations were repeated every week. After the first, third and sixth in vitro stimulation, CTL lines were tested for their avidity for the native MAGE-$A_{248D9}$ peptide in a classical $^{51}$Cr release cytotoxicity assay (Table 6).

TABLE 6

Avidity of CTL lines established from MAGE-$A_{248V9}$ primed spleen cells in vitro stimulated with either MAGE-$A_{248V9}$ or MAGE-$A_{248D9}$ peptides

| No of in vitro stimulations | Peptide used for the in vitro stimulation | CTL avidity (nM) |
|---|---|---|
| 1 | MAGE-$A_{248D9}$ | 200 |
| | MAGE-$A_{248V9}$ | 400 |
| 3 | MAGE-$A_{248D9}$ | 40 |
| | MAGE-$A_{248V9}$ | 450 |
| 6 | MAGE-$A_{248D9}$ | 0.8 |
| | MAGE-$A_{248V9}$ | 320 |

2.3. Conclusion

Vaccination with optimized cryptic peptides recruits a CTL repertoire that contains cells with high avidity for the native cryptic peptide. These high avidity CTL can be in vitro selected and amplified by stimulation with the native rather than with the optimized cryptic peptide.

Example 3

In Vivo Selection of CTLs with High Avidity by Boosting with the Native Peptide 3.1. Materials and Methods The same materials and methods as in Example 2 were used.

3.2. Results

HHD mice were vaccinated with the optimized cryptic $TERT_{572Y}$ peptide described above. Fifteen days later, they were boosted with either the same optimized or the native cryptic $TERT_{572}$ peptide. Seven days after the boost, their spleen cells were in vitro stimulated with 10 µM of the $TERT_{572}$. CTL generated after one cycle of in vitro stimulation were tested for their avidity for $TERT_{572}$. Table 7 presents results from six individual mice.

TABLE 7

Avidity of CTL generated in HHD mice primed with the optimized cryptic $TERT_{572Y}$ peptide and boosted with either the same optimized or the native $TERT_{572}$ peptide.

| Mouse | 1st vaccination | 2nd vaccination | CTL avidity (nM) |
|---|---|---|---|
| 1 | $TERT_{572Y}$ | $TERT_{572Y}$ | 350 |
| 2 | $TERT_{572Y}$ | $TERT_{572Y}$ | 700 |
| 3 | $TERT_{572Y}$ | $TERT_{572Y}$ | 650 |
| 1 | $TERT_{572Y}$ | $TERT_{572}$ | 110 |
| 2 | $TERT_{572Y}$ | $TERT_{572}$ | 190 |
| 3 | $TERT_{572Y}$ | $TERT_{572}$ | 70 |

3.3. Conclusion

In vivo priming with the optimized cryptic peptides recruits a repertoire containing CTL with high avidity for the native peptide. These high avidity CTLs can be in vivo selected and amplified by boosting with the native rather than with the optimized peptide.

Example 4

Tumor Immunity in HHD Mice 4.1. Materials and Methods

The same materials and methods as in Example 2 were used.

An additional peptide, named $gp100_{154}$, was also used: KTWGQYWQV (SEQ ID NO: 8).

4.2. Results

HHD mice were vaccinated with the optimized cryptic $TERT_{572Y}$ and $TERT_{988Y}$ peptides and fifteen days later boosted with either the same optimized or the corresponding native cryptic peptide. Ten days after the boost, mice were challenged with EL4/HHD tumor cells and monitored for tumor growth and survival. Mice primed and boosted with the $gp100_{154}$ peptide were used as negative controls (Table 8). 100% of control mice died by day 43 post-challenge. 17% of mice primed and boosted with the optimized peptides and 50% of mice primed with the optimized and boosted with the native peptide were definitively protected against tumor.

TABLE 8

Survival of HHD mice primed with the optimized and boosted with either the same optimized or the corresponding native peptides.

| Prime | Boost | Survival post-challenge (days) |
|---|---|---|
| $Gp100_{154}$ | $Gp100_{154}$ | 41 |
| | | 40 |
| | | 39 |
| | | 39 |
| | | 43 |
| | | 41 |
| $TERT_{572Y}$ | $TERT_{572Y}$ | 31 |
| | | 40 |
| | | 40 |
| | | 40 |
| | | 200+ |
| | | 45 |
| $TERT_{572Y}$ | $TERT_{572}$ | 200+ |
| | | 200+ |
| | | 32 |
| | | 35 |
| | | 200+ |
| | | 40 |
| $TERT_{988Y}$ | $TERT_{988Y}$ | 200+ |
| | | 40 |
| | | 40 |
| | | 40 |
| | | 43 |
| | | 43 |
| $TERT_{988Y}$ | $TERT_{988}$ | 39 |
| | | 40 |
| | | 41 |
| | | 200+ |
| | | 200+ |
| | | 200+ |

4.3. Conclusion

Tumor immunity is much more efficient in mice primed with the optimized and boosted with the native peptide than in mice primed and boosted with the same optimized peptide.

References

Ajani, J. A., S. R. Welch, et al. (1990). "Comprehensive criteria for assessing therapy-induced toxicity." *Cancer Invest* 8(2): 147-59.

Ayyoub, M., M. Migliaccio, et al. (2001). "Lack of tumor recognition by hTERT peptide 540-548-specific CD8(+) T cells from melanoma patients reveals inefficient antigen processing." *Eur J Immunol* 31(9): 2642-51.

Bakker, A. B., S. H. van der Burg, et al. (1997). "Analogues of CTL epitopes with improved MHC class-I binding capacity elicit anti-melanoma CTL recognizing the wild-type epitope." *Int J Cancer* 70(3): 302-9.

Cheever, M. A. and W. Chen (1997). "Therapy with cultured T cells: principles revisited." *Immunol Rev* 157: 177-94.

Cibotti, R., J. M. Kanellopoulos, et al. (1992). "Tolerance to a self-protein involves its immunodominant but does not involve its subdominant determinants." *Proc Natl Acad Sci USA* 89(1): 416-20.

Clay, T. M., M. C. Custer, et al. (1999). "Changes in the fine specificity of gp100(209-217)-reactive T cells in patients following vaccination with a peptide modified at an HLA-A2.1 anchor residue." *J Immunol* 162(3): 1749-55.

Colella, T. A., T. N. Bullock, et al. (2000). "Self-tolerance to the murine homologue of a tyrosinase-derived melanoma antigen: implications for tumor immunotherapy." *J Exp Med* 191(7): 1221-32.

Disis, M. L., T. A. Gooley, et al. (2002). "Generation of T-cell immunity to the HER-2/neu protein after active immunization with HER-2/neu peptide-based vaccines." *J Clin Oncol* 20(11): 2624-32.

Disis, M. L., K. Schiffman, et al. (2004). "Effect of dose on immune response in patients vaccinated with an her-2/neu intracellular domain protein-based vaccine." *J Clin Oncol* 22(10): 1916-25.

Gross, D. A., S. Graff-Dubois, et al. (2004). "High vaccination efficiency of low-affinity epitopes in antitumor immunotherapy." *J Clin Invest* 113(3): 425-33.

Grossmann, M. E., E. Davila, et al. (2001). "Avoiding Tolerance Against Prostatic Antigens With Subdominant Peptide Epitopes." *J Immunother* 24(3): 237-241.

Hernandez, J., F. Garcia-Pons, et al. (2002). "Identification of a human telomerase reverse transcriptase peptide of low affinity for HLA A2.1 that induces cytotoxic T lymphocytes and mediates lysis of tumor cells." *Proc Natl Acad Sci USA* 99(19): 12275-80.

Hernandez, J., P. P. Lee, et al. (2000). "The use of HLA A2.1/p53 peptide tetramers to visualize the impact of self tolerance on the TCR repertoire." *J Immunol* 164(2): 596-602.

Kim, N. W., M. A. Piatyszek, et al. (1994). "Specific association of human telomerase activity with immortal cells and cancer." *Science* 266(5193): 2011-5.

Knutson, K. L., K. Schiffman, et al., (2002). "Immunization of cancer patients with a HER-2/neu, HLA-A2 peptide, p 369-377, results in short-lived peptide-specific immunity." *Clin Cancer Res* 8(5): 1014-8.

Liu, K., M. M. Schoonmaker, et al., (1999). "Constitutive and regulated expression of telomerase reverse transcriptase (hTERT) in human lymphocytes." *Proc Natl Acad Sci USA* 96(9): 5147-52.

Miller, A. B., B. Hoogstraten, et al., (1981). "Reporting results of cancer treatment." *Cancer* 47(1): 207-14.

Minev, B., J. Hipp, et al. (2000). "Cytotoxic T cell immunity against telomerase reverse transcriptase in humans." *Proc Natl Acad Sci USA* 97(9): 4796-801.

Moudgil, K. D. and E. E. Sercarz (1994). "Can antitumor immune responses discriminate between self and non-self?" *Immunol Today* 15(8): 353-5.

Parkhurst, M. R., J. P. Riley, et al. (2004). "Immunization of patients with the hTERT:540-548 peptide induces peptide-reactive T lymphocytes that do not recognize tumors endogenously expressing telomerase." *Clin Cancer Res* 10(14): 4688-98.

Parkhurst, M. R., M. L. Salgaller, et al. (1996). "Improved induction of melanoma-reactive CTL with peptides from the melanoma antigen gp100 modified at HLA-A*0201-binding residues." *J Immunol* 157(6): 2539-48.

Pascolo, S., N. Bervas, et al. (1997). "HLA-A2.1-restricted education and cytolytic activity of CD8(+) T lymphocytes from beta2 microglobulin (beta2m) HLA-A2.1 monochain transgenic H-2 Db beta2m double knockout mice." *J Exp Med* 185(12): 2043-51.

Pullarkat, V., P. P. Lee, et al. (2003). "A phase I trial of SD-9427 (progenipoietin) with a multipeptide vaccine for resected metastatic melanoma." *Clin Cancer Res* 9(4): 1301-12.

Ramakrishnan, S., U. Eppenberger, et al. (1998). "Expression profile of the putative catalytic subunit of the telomerase gene." *Cancer Res* 58(4): 622-5.

Scardino, A., D. A. Gross, et al. (2002). "HER-2/neu and hTERT cryptic epitopes as novel targets for broad spectrum tumor immunotherapy." *J Immunol* 168(11): 5900-6.

Schaed, S. G., V. M. Klimek, et al. (2002). "T-cell responses against tyrosinase 368-376(370D) peptide in HLA*A0201+ melanoma patients: randomized trial comparing incomplete Freund's adjuvant, granulocyte macrophage colony-stimulating factor, and QS-21 as immunological adjuvants." *Clin Cancer Res* 8(5): 967-72.

Scheibenbogen, C., K. H. Lee, et al. (1997). "Analysis of the T cell response to tumor and viral peptide antigens by an IFNgamma-ELISPOT assay." *Int J Cancer* 71(6): 932-6.

Slingluff, C. L., Jr., G. R. Petroni, et al. (2003). "Clinical and immunologic results of a randomized phase II trial of vaccination using four melanoma peptides either administered in granulocyte-macrophage colony-stimulating factor in adjuvant or pulsed on dendritic cells." *J Clin Oncol* 21(21): 4016-26.

Slingluff, C. L., Jr., G. Yamshchikov, et al. (2001). "Phase I trial of a melanoma vaccine with gp100(280-288) peptide and tetanus helper peptide in adjuvant: immunologic and clinical outcomes." *Clin Cancer Res* 7(10): 3012-24.

Theobald, M., J. Biggs, et al. (1997). "Tolerance to p53 by A2.1-restricted cytotoxic T lymphocytes." *J Exp Med* 185 (5): 833-41.

Tourdot, S., A. Scardino, et al. (2000). "A general strategy to enhance immunogenicity of low-affinity HLA-A2.1-associated peptides: implication in the identification of cryptic tumor epitopes." *Eur J Immunol* 30(12): 3411-21.

Valmori, D., J. F. Fonteneau, et al. (1998). "Enhanced generation of specific tumor-reactive CTL in vitro by selected Melan-A/MART-1 immunodominant peptide analogues." *J Immunol* 160(4): 1750-8.

Vonderheide, R. H., S. M. Domchek, et al. (2004). "Vaccination of cancer patients against telomerase induces functional antitumor CD8+ T lymphocytes." *Clin Cancer Res* 10(3): 828-39.

Vonderheide, R. H., W. C. Hahn, et al. (1999). "The telomerase catalytic subunit is a widely expressed tumor-associated antigen recognized by cytotoxic T lymphocytes." *Immunity* 10(6): 673-9.

---

The invention claimed is:

1. A method for selecting, in a CTL immune response initiated by a cognate optimized peptide, CTLs having a high avidity for a native peptide, comprising vaccinating a patient, who has been previously vaccinated with said cognate optimized peptide, with a medicinal composition containing the native peptide from which said cognate optimized peptide was derived, wherein the native and its cognate optimized peptides are selected from the group consisting of the following pairs of peptides:

TERT572 (SEQ ID No: 1) and TERT572Y1 (SEQ ID No: 2);
TERT988 (SEQ ID No: 3) and TERT988Y1 (SEQ ID No: 4);
MAGE-A248D9 (SEQ ID No: 5) and MAGE-A248V9 (SEQ ID No: 6);
MAGE-A248G9 (SEQ ID No: 7) and MAGE-A248V9 (SEQ ID No: 6);
Gp100 154 (SEQ ID No: 8) and Gp100 154Y1 (SEQ ID No: 9);
Gp100 154 (SEQ ID No: 8) and Gp100 154M155 (SEQ ID No: 10);
FluM58 (SEQ ID No: 11) and FluM58Y1 (SEQ ID No: 12);
HIVgag76 (SEQ ID No: 13) and HIVgag76Y1 (SEQ ID No: 14);
HBVpo1575 (SEQ ID No: 15) and HBVpo1575Y1 (SEQ ID No: 16);
HBVpo1765 (SEQ ID No: 17) and HBVpo1765Y1 (SEQ ID No: 18);
Mart-127 (SEQ ID No: 19) and Mart-127Y1 (SEQ ID No: 20);
Mart-126 (SEQ ID No: 21) and Mart-126L27 (SEQ ID No: 22);
Gp100 177 (SEQ ID No: 23) and Gp100 177Y1 (SEQ ID No: 24);
Gp100 178 (SEQ ID No: 25) and Gp100 178Y1 (SEQ ID No: 26);
Gp100 570 (SEQ ID No: 27) and Gp100 570Y1 (SEQ ID No: 28);
Gp100 209 (SEQ ID No: 29) and Gp100 209Y1 (SEQ ID No: 30);
Gp100 209 (SEQ ID No: 29) and Gp100 209M210 (SEQ ID No: 31);
Gp100 476 (SEQ ID No: 32) and Gp100 476Y1 (SEQ ID No: 33);
Gp100 457 (SEQ ID No: 34) and Gp100 457Y1 (SEQ ID No: 35);
HER-2/neu799 (SEQ ID No: 36) and HER-2/neu799Y1 (SEQ ID No: 37);
HER-2/neu369 (SEQ ID No: 38) and HER-2/neu369Y1 (SEQ ID No: 39);
HER-2/neu789 (SEQ ID No: 40) and HER-2/neu789Y1 (SEQ ID No: 41);
HER-2/neu48 (SEQ ID No: 42) and HER-2/neu48Y1 (SEQ ID No: 43);
HER-2/neu773 (SEQ ID No: 44) and HER-2/neu773Y1 (SEQ ID No: 45)-;
HER-2/neu5 (SEQ ID No: 46) and HER-2/neu5Y1 (SEQ ID No: 47);
HER-2/neu851 (SEQ ID No: 48) and HER-2/neu851Y1 (SEQ ID No: 49);
HER-2/neu661 (SEQ ID No: 50) and HER-2/neu661Y1 (SEQ ID No: 51);
HER-2/neu650 (SEQ ID No: 52) and HER-2/neu650Y1 (SEQ ID No: 53);
HER-2/neu466 (SEQ ID No: 54) and HER-2/neu466Y1 (SEQ ID No: 55);
HER-2/neu402 (SEQ ID No: 56) and HER-2/neu402Y1 (SEQ ID No: 57);
HER-2/neu391 (SEQ ID No: 58) and HER-2/neu391Y1 (SEQ ID No: 59);
HER-2/neu971 (SEQ ID No: 60) and HER-2/neu971Y1 (SEQ ID No: 61);
HBVpo128 (SEQ ID No: 62) and HBVpo128Y1 (SEQ ID No: 63);
HBVpo1594 (SEQ ID No: 64) and HBVpo1594Y1 (SEQ ID No: 65);
HBVpo1985 (SEQ ID No: 66) and HBVpo1985Y1 (SEQ ID No: 67);
EphA2 61 (SEQ ID No: 68) and EphA2 61Y1 (SEQ ID No: 69);
HER2 911 (SEQ ID No: 70) and HER911Y1V10 (SEQ ID No: 71);
HER4 911 (SEQ ID No: 72) and HER911Y1V10 (SEQ ID No: 71);
HER1 911 (SEQ ID No: 73) and HER911Y1V10 (SEQ ID No: 71);
HER2 722 (SEQ ID No: 74) and HER722Y1V9 (SEQ ID No: 75);
HER3 722 (SEQ ID No: 76) and HER722Y1V9 (SEQ ID No: 75);
HER4 722 (SEQ ID No: 77) and HER722Y1V9 (SEQ ID No: 75);
HER1 722 (SEQ ID No: 78) and HER722Y1V9 (SEQ ID No: 75);
HER2 845 (SEQ ID No: 79) and HER845Y1 (SEQ ID No: 80);
HER3 845 (SEQ ID No: 81) and HER845Y1 (SEQ ID No: 80);
HER2 904 (SEQ ID No: 82) and HER904Y1 (SEQ ID No: 83);
HER4 904 (SEQ ID No: 84) and HER904Y1 (SEQ ID No: 83);
HER2 933 (SEQ ID No: 85) and HER933Y1 (SEQ ID No: 86);
HER1 933 (SEQ ID No: 87) and HER933Y1 (SEQ ID No: 86);
HER2 945 (SEQ ID No: 88) and HER945Y1 (SEQ ID No: 90);
HER3 945 (SEQ ID No: 89) and HER945Y1 (SEQ ID No: 90)-;
HER4 945 (SEQ ID No: 91) and HER945Y1 (SEQ ID No: 90); and
HER1 945 (SEQ ID No: 92) and HER945Y1 (SEQ ID No: 90).

2. The method of claim 1, wherein the native peptide is a cryptic peptide.

3. The method of claim 2, wherein the native cryptic peptide is TERT572 (RLFFYRKSV, SEQ ID No: 1) and its cognate optimized peptide is TERT572Y (YLFFYRKSV, SEQ ID No: 2).

4. The method of claim 2, wherein the native cryptic peptide is TERT988 (DLQVNSLQTV, SEQ ID No: 3) and its cognate optimized peptide is TERT988Y (YLQVNSLQTV, SEQ ID No: 4).

5. The method of claim 2, wherein the native cryptic peptide is MAGE-A248D9 (YLEYRQVPD, SEQ ID No: 5) or MAGE-A248G9 (YLEYRQVPG, SEQ ID No: 7) and its cognate optimized peptide is MAGE-A248V9 (YLEYRQVPV, SEQ ID No: 6).

6. A method for vaccinating a patient against a tumoral or viral antigen comprising a first step of vaccination with an optimized peptide cognate to a native peptide of said antigen, followed by a second step of vaccination with said native peptide, wherein said native and cognate optimized peptides are selected from the group consisting of the following pairs of peptides:

TERT572 (SEQ ID No: 1) and TERT572Y1 (SEQ ID No: 2);

TERT988 (SEQ ID No: 3) and TERT988Y1 (SEQ ID No: 4);

MAGE-A248D9 (SEQ ID No: 5) and MAGE-A248V9 (SEQ ID No: 6);

MAGE-A248G9 (SEQ ID No: 7) and MAGE-A248V9 (SEQ ID No: 6);

Gp100 154 (SEQ ID No: 8) and Gp100 154Y1 (SEQ ID No: 9);

Gp100 154 (SEQ ID No: 8) and Gp100 154M155 (SEQ ID No: 10);

FluM58 (SEQ ID No: 11) and FluM58Y1 (SEQ ID No: 12);

HIVgag76 (SEQ ID No: 13) and HIVgag76Y1 (SEQ ID No: 14);

HBVpo1575 (SEQ ID No: 15) and HBVpo1575Y1 (SEQ ID No: 16);

HBVpo1765 (SEQ ID No: 17) and HBVpo1765Y1 (SEQ ID No: 18);

Mart-127 (SEQ ID No: 19) and Mart-127Y1 (SEQ ID No: 20);

Mart-126 (SEQ ID No: 21) and Mart-126L27 (SEQ ID No: 22);

Gp100 177 (SEQ ID No: 23) and Gp100 177Y1 (SEQ ID No: 24);

Gp100 178 (SEQ ID No: 25) and Gp100 178Y1 (SEQ ID No: 26);

Gp100 570 (SEQ ID No: 27) and Gp100 570Y1 (SEQ ID No: 28);

Gp100 209 (SEQ ID No: 29) and Gp100 209Y1 (SEQ ID No: 30);

Gp100 209 (SEQ ID No: 29) and Gp100 209M210 (SEQ ID No: 31);

Gp100 476 (SEQ ID No: 32) and Gp100 476Y1 (SEQ ID No: 33);

Gp100 457 (SEQ ID No: 34) and Gp100 457Y1 (SEQ ID No: 35);

HER-2/neu799 (SEQ ID No: 36) and HER-2/neu799Y1 (SEQ ID No: 37);

HER-2/neu369 (SEQ ID No: 38) and HER-2/neu369Y1 (SEQ ID No: 39);

HER-2/neu789 (SEQ ID No: 40) and HER-2/neu789Y1 (SEQ ID No: 41);

HER-2/neu48 (SEQ ID No: 42) and HER-2/neu48Y1 (SEQ ID No: 43);

HER-2/neu773 (SEQ ID No: 44) and HER-2/neu773Y1 (SEQ ID No: 45);

HER-2/neu5 (SEQ ID No: 46) and HER-2/neu5Y1 (SEQ ID No: 47);

HER-2/neu851 (SEQ ID No: 48) and HER-2/neu851Y1 (SEQ ID No: 49);

HER-2/neu661 (SEQ ID No: 50) and HER-2/neu661Y1 (SEQ ID No: 51);

HER-2/neu650 (SEQ ID No: 52) and HER-2/neu650Y1 (SEQ ID No: 53);

HER-2/neu466 (SEQ ID No: 54) and HER-2/neu466Y1 (SEQ ID No: 55);

HER-2/neu402 (SEQ ID No: 56) and HER-2/neu402Y1 (SEQ ID No: 57);

HER-2/neu391 (SEQ ID No: 58) and HER-2/neu391Y1 (SEQ ID No: 59);

HER-2/neu971 (SEQ ID No: 60) and HER-2/neu971Y1 (SEQ ID No: 61);

HBVpo128 (SEQ ID No: 62) and HBVpo128Y1 (SEQ ID No: 63);

HBVpo1594 (SEQ ID No: 64) and HBVpo1594Y1 (SEQ ID No: 65);

HBVpo1985 (SEQ ID No: 66) and HBVpo1985Y1 (SEQ ID No: 67);

EphA2 61 (SEQ ID No: 68) and EphA2 61Y1 (SEQ ID No: 69);

HER2 911 (SEQ ID No: 70) and HER911Y1V10 (SEQ ID No: 71);

HER4 911 (SEQ ID No: 72) and HER911Y1V10 (SEQ ID No: 71);

HER1 911 (SEQ ID No: 73) and HER911Y1V10 (SEQ ID No: 71);

HER2 722 (SEQ ID No: 74) and HER722Y1V9 (SEQ ID No: 75);

HER3 722 (SEQ ID No: 76) and HER722Y1V9 (SEQ ID No: 75);

HER4 722 (SEQ ID No: 77) and HER722Y1V9 (SEQ ID No: 75);

HER1 722 (SEQ ID No: 78) and HER722Y1V9 (SEQ ID No: 75);

HER2 845 (SEQ ID No: 79) and HER845Y1 (SEQ ID No: 80);

HER3 845 (SEQ ID No: 81) and HER845Y1 (SEQ ID No: 80);

HER2 904 (SEQ ID No: 82) and HER904Y1 (SEQ ID No: 83);

HER4 904 (SEQ ID No: 84) and HER904Y1 (SEQ ID No: 83);

HER2 933 (SEQ ID No: 85) and HER933Y1 (SEQ ID No: 86);

HER1 933 (SEQ ID No: 87) and HER933Y1 (SEQ ID No: 86);

HER2 945 (SEQ ID No: 88) and HER945Y1 (SEQ ID No: 90);

HER3 945 (SEQ ID No: 89) and HER945Y1 (SEQ ID No: 90);

HER4 945 (SEQ ID No: 91) and HER945Y1 (SEQ ID No: 90); and

HER1 945 (SEQ ID No: 92) and HER945Y1 (SEQ ID No: 90), wherein the step of vaccination with the native peptide amplifies CTLs with high avidity for said native peptide.

7. The method of claim 6, wherein the first step includes two vaccinations with said cognate optimized peptide and the second step includes four vaccinations with said native peptide.

8. A method for amplifying CTLs with high avidity for a native peptide in a patient who has been immunized with an optimized peptide cognate to said native peptide, comprising vaccinating said patient with a medicinal composition containing the native peptide, wherein said native and cognate optimized peptides are selected from the group consisting of the following pairs of peptides:

TERT572 (SEQ ID No: 1) and TERT572Y1 (SEQ ID No: 2);

TERT988 (SEQ ID No: 3) and TERT988Y1 (SEQ ID No: 4);

MAGE-A248D9 (SEQ ID No: 5) and MAGE-A248V9 (SEQ ID No: 6);

MAGE-A248G9 (SEQ ID No: 7) and MAGE-A248V9 (SEQ ID No: 6);

Gp100 154 (SEQ ID No: 8) and Gp100 154Y1 (SEQ ID No: 9);

Gp100 154 (SEQ ID No: 8) and Gp100 154M155 (SEQ ID No: 10);

FluM58 (SEQ ID No: 11) and FluM58Y1 (SEQ ID No: 12);

HIVgag76 (SEQ ID No: 13) and HIVgag76Y1 (SEQ ID No: 14);

HBVpo1575 (SEQ ID No: 15) and EIBVpo1575Y1 (SEQ ID No: 16);

HBVpo1765 (SEQ ID No: 17) and HBVpo1765Y1 (SEQ ID No: 18);

Mart-127 (SEQ ID No: 19) and Mart-127Y1 (SEQ ID No: 20);

Mart-126 (SEQ ID No: 21) and Mart-126L27 (SEQ ID No: 22);

Gp100 177 (SEQ ID No: 23) and Gp100 177Y1 (SEQ ID No: 24);

Gp100 178 (SEQ ID No: 25) and Gp100 178Y1 (SEQ ID No: 26);

Gp100 570 (SEQ ID No: 27) and Gp100 570Y1 (SEQ ID No: 28);

Gp100 209 (SEQ ID No: 29) and Gp100 209Y1 (SEQ ID No: 30);

Gp100 209 (SEQ ID No: 29) and Gp100 209M210 (SEQ ID No: 31);

Gp100 476 (SEQ ID No: 32) and Gp100 476Y1 (SEQ ID No: 33);

Gp100 457 (SEQ ID No: 34) and Gp100 457Y1 (SEQ ID No: 35);

HER-2/neu799 (SEQ ID No: 36) and HER-2/neu799Y1 (SEQ ID No: 37);

HER-2/neu369 (SEQ ID No: 38) and HER-2/neu369Y1 (SEQ ID No: 39);

HER-2/neu789 (SEQ ID No: 40) and HER-2/neu789Y1 (SEQ ID No: 41);

HER-2/neu48 (SEQ ID No: 42) and HER-2/neu48Y1 (SEQ ID No: 43);

HER-2/neu773 (SEQ ID No: 44) and HER-2/neu773Y1 (SEQ ID No: 45);

HER-2/neu5 (SEQ ID No: 46) and HER-2/neu5Y1 (SEQ ID No: 47);

HER-2/neu851 (SEQ ID No: 48) and HER-2/neu851Y1 (SEQ ID No: 49);

HER-2/neu661 (SEQ ID No: 50) and HER-2/neu661Y1 (SEQ ID No: 51);

HER-2/neu650 (SEQ ID No: 52) and HER-2/neu650Y1 (SEQ ID No: 53);

HER-2/neu466 (SEQ ID No: 54) and HER-2/neu466Y1 (SEQ ID No: 55);

HER-2/neu402 (SEQ ID No: 56) and HER-2/neu402Y1 (SEQ ID No: 57);

HER-2/neu391 (SEQ ID No: 58) and HER-2/neu391Y1 (SEQ ID No: 59);

HER-2/neu971 (SEQ ID No: 60) and HER-2/neu971Y1 (SEQ ID No: 61);

HBVpo128 (SEQ ID No: 62) and HBVpo128Y1 (SEQ ID No: 63);

HBVpo1594 (SEQ ID No: 64) and HBVpo1594Y1 (SEQ ID No: 65);

HBVpo1985 (SEQ ID No: 66) and HBVpo1985Y1 (SEQ ID No: 67);

EphA2 61 (SEQ ID No: 68) and EphA2 61Y1 (SEQ ID No: 69);

HER2 911 (SEQ ID No: 70) and HER911Y1V10 (SEQ ID No: 71);

HER4 911 (SEQ ID No: 72) and HER911Y1V10 (SEQ ID No: 71);

HER1 911 (SEQ ID No: 73) and HER911Y1V10 (SEQ ID No: 71);

HER2 722 (SEQ ID No: 74) and HER722Y1V9 (SEQ ID No: 75);

HER3 722 (SEQ ID No: 76) and HER722Y1V9 (SEQ ID No: 75);

HER4 722 (SEQ ID No: 77) and HER722Y1V9 (SEQ ID No: 75);

HER1 722 (SEQ ID No: 78) and HER722Y1V9 (SEQ ID No: 75);

HER2 845 (SEQ ID No: 79) and HER845Y1 (SEQ ID No: 80);

HER3 845 (SEQ ID No: 81) and HER845Y1 (SEQ ID No: 80);

HER2 904 (SEQ ID No: 82) and HER904Y1 (SEQ ID No: 83);

HER4 904 (SEQ ID No: 84) and HER904Y1 (SEQ ID No: 83);

HER2 933 (SEQ ID No: 85) and HER933Y1 (SEQ ID No: 86);

HER1 933 (SEQ ID No: 87) and HER933Y1 (SEQ ID No: 86);

HER2 945 (SEQ ID No: 88) and HER945Y1 (SEQ ID No: 90);

HER3 945 (SEQ ID No: 89) and HER945Y1 (SEQ ID No: 90);

HER4 945 (SEQ ID No: 91) and HER945Y1 (SEQ ID No: 90); and

HER1 945 (SEQ ID No: 92) and HER945Y1 (SEQ ID No: 90).

9. The method of claim 8, wherein the native peptide is a cryptic peptide.

* * * * *